United States Patent
Watson et al.

(10) Patent No.: US 9,453,073 B2
(45) Date of Patent: Sep. 27, 2016

(54) ANTI-GLUCAGON ANTIBODIES AND USES THEREOF

(71) Applicant: Eli Lilly and Company, Indianapolis, IN (US)

(72) Inventors: David Edward Watson, Indianapolis, IN (US); Robert W. Siegel, Fountaintown, IN (US); Nan Jia, West Lebanon, NH (US); John Harrison Sloan, Zionsville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/361,017

(22) PCT Filed: Nov. 27, 2012

(86) PCT No.: PCT/US2012/066587
§ 371 (c)(1),
(2) Date: May 28, 2014

(87) PCT Pub. No.: WO2013/081993
PCT Pub. Date: Jun. 6, 2013

(65) Prior Publication Data
US 2014/0335096 A1    Nov. 13, 2014

Related U.S. Application Data

(60) Provisional application No. 61/566,080, filed on Dec. 2, 2011.

(51) Int. Cl.
| | | |
|---|---|---|
| A61K 39/00 | (2006.01) | |
| C07K 16/26 | (2006.01) | |
| G01N 33/577 | (2006.01) | |

(52) U.S. Cl.
CPC ............. *C07K 16/26* (2013.01); *G01N 33/577* (2013.01); *C07K 2317/565* (2013.01); *C07K 2317/75* (2013.01); *C07K 2317/92* (2013.01)

(58) Field of Classification Search
CPC .......................... C07K 16/26; C07K 2317/565
See application file for complete search history.

(56) References Cited

U.S. PATENT DOCUMENTS 4,312,943 A     1/1982 Iwasa et al.

FOREIGN PATENT DOCUMENTS

| WO | 2007/124463 | 11/2007 |
| WO | 2009/120530 | 10/2009 |

OTHER PUBLICATIONS

John H. Sloan et al, "A novel high-sensitivity electrochemilunninescence (ECL) sandwich immunoassay for the specific quantitative measurement of plasma glucagon", Clinical Biochemistry, vol. 45, No. 18, Aug. 4, 2012.
Brand C. L. et al, "Immunoneutralization of endogenous glucagon with monoclonal glucagon antibody normalizes hyperglycaemia in moderately streptozotocin-diabetic rats", Diabetologia, Springer, Berlin, DE, vol. 37, No. 10, Jan. 1, 1994.
Christelle Guillo et al, "Simultaneous capillary electrophoresis competitive immunoassay for insulin, glucagon, and islet amyloid polypeptide secretion from mouse islets of Langerhans", Journal of Chromatography, Elsevier Science Publishers B.V, NL, vol. 1218, No. 26, May 6, 2011.
Witt S. et al, Production and use of monoclonal glucagon and insulin antibodies—reduction of pancreatic insulin in rats by treatment with complete Freund's adjuvant. Acta Histochemica, Supplement (1988) 35: 217-223.
Guoqiang, Jiang. et al. Glucagon and regulation of glucose metabolism. American Journal Physiology Endocrinology Metabolism (2003) 284: E671-E678.
Sloop, M. et al. Role of the glucagon receptor in glucose homeostasis: a therapeutic target to improve glycemic control of T2D. Drugs of the Future (2004) 29(8), 835-841.

*Primary Examiner* — Gyan Chandra
(74) *Attorney, Agent, or Firm* — Dan L. Wood

(57) ABSTRACT

Provided are monoclonal antibodies, or antigen-binding fragments thereof, that bind to glucagon. These antibodies are useful in immunoassays of glucagon levels, and/or in vivo, ex vivo or in vitro immunochemical and other imaging methods for detecting glucagon levels, and for diagnostic, prognostic and predictive purposes, and for optimizing therapeutic regimens in patients in which glucagon signaling is implicated in pathogenesis.

8 Claims, 4 Drawing Sheets

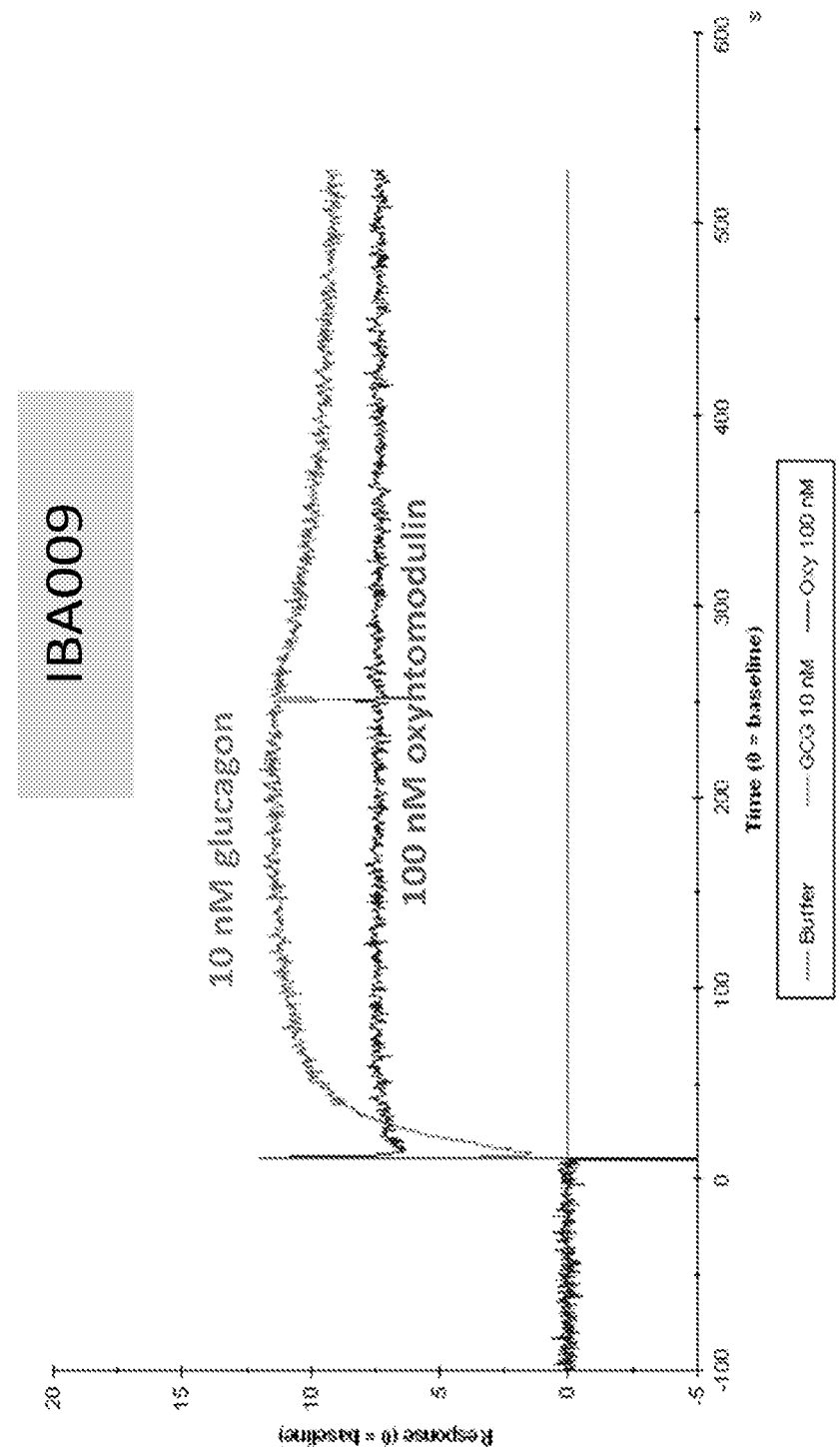

SEQUENCE LISTING

<160> NUMBER OF SEQ ID NOS: 29

<210> SEQ ID NO 1
<211> LENGTH: 11
<212> TYPE: PRT
<213> ORGANISM: Artificial Sequence
<220> FEATURE:
<223> OTHER INFORMATION: Synthetic

<400> SEQUENCE: 1

Lys Ala Ser Glu Asn Ala Gly Thr Tyr Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Asn Gly Ser His Arg Tyr Asp
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic

<400> SEQUENCE: 3

Gly Gln Ser Tyr Ser Tyr Pro Trp Thr
1               5

<210> SEQ ID NO 4
<211> LENGTH: 10
<212> TYPE: PRT
<213> ORGANISM: Artificial Sequence
<220> FEATURE:
<223> OTHER INFORMATION: Synthetic

<400> SEQUENCE: 4

Gly Tyr Asn Phe Asn Asp Tyr Trp Leu Asn
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthetic

<400> SEQUENCE: 5

Asn Ala Tyr Pro Gly Trp Gly Ile Ile Asn Tyr Asn Glu Lys Phe Lys
1               5                   10                  15

Ser

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Asp Tyr Asp Asn Ala Tyr
1               5

<210> SEQ ID NO 7
<211> LENGTH: 108
<212> TYPE: PRT
<213> ORGANISM: Artificial Sequence
<220> FEATURE:
<223> OTHER INFORMATION: Synthetic

<400> SEQUENCE: 7

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Ala Gly Thr Tyr
            20                  25                  30

Val Ala Trp Tyr Gln Gln Lys Pro Glu Gln Ser Pro Lys Leu Leu Ile
        35                  40                  45

Tyr Asn Gly Ser His Arg Tyr Asp Gly Val Pro Asp Arg Phe Thr Gly
    50                  55                  60

Ser Gly Ser Ala Thr Asp Phe Thr Leu Thr Ile Ser Ser Val Gln Ala
65                  70                  75                  80

Glu Asp Leu Ala Asp Tyr Tyr Cys Gly Gln Ser Tyr Ser Tyr Pro Trp
                85                  90                  95

Thr Phe Gly Gly Gly Thr Lys Leu Glu Met Lys Arg
                100                 105

<210> SEQ ID NO 8
<211> LENGTH: 324
<212> TYPE: DNA
<213> ORGANISM: Artificial Sequence
<220> FEATURE:
<223> OTHER INFORMATION: Synthetic

<400> SEQUENCE: 8
aacattgtga tgacccagag cccgaaaagc atgagcatga gcgtgggcga acgtgtgacc        60
ctgacctgca aagcgagcga gaacgctggc acctatgttg cgtggtatca gcagaaaccg       120
gaacagtctc cgaaactgct gatctataat gggagccacc ggtatgacgg cgtgccggat       180
cgttttaccg gcagcggcag cgcgaccgat ttcaccctga ccattagcag cgtgcaggcg       240
gaagatctgg cggattatta ctgcggccag agctatagct atccgtggac ctttggcggt       300
gggaccaagc tggaaatgaa acgg                                              324

<210> SEQ ID NO 9
<211> LENGTH: 115
<212> TYPE: PRT
<213> ORGANISM: Artificial Sequence
<220> FEATURE:
<223> OTHER INFORMATION: Synthetic

<400> SEQUENCE: 9

Gln Val Gln Leu Leu Gln Pro Gly Ala Glu Leu Val Lys Pro Gly Ala
1               5                   10                  15

Ser Val Lys Leu Ser Cys Lys Ala Ser Gly Tyr Asn Phe Asn Asp Tyr
            20                  25                  30

Trp Leu Asn Trp Val Lys Gln Arg Pro Gly Gln Gly Leu Glu Trp Ile
        35                  40                  45

Gly Asn Ala Tyr Pro Gly Trp Gly Ile Ile Asn Tyr Asn Glu Lys Phe
    50                  55                  60

Lys Ser Lys Val Thr Leu Thr Val Asp Thr Ser Ser Ser Thr Val Tyr

```
                65                  70                  75                  80
Met Gln Leu Ser Ser Leu Thr Ser Asp Asp Ser Ala Val Tyr Tyr Cys
                    85                  90                  95

Ala Arg Asp Tyr Asp Asn Ala Tyr Trp Gly Gln Gly Thr Thr Val Thr
                100                 105                 110

Val Ser Ser
        115

<210> SEQ ID NO 10
<211> LENGTH: 345
<212> TYPE: DNA
<213> ORGANISM: Artificial Sequence
<220> FEATURE:
<223> OTHER INFORMATION: Synthetic

<400> SEQUENCE: 10
caggtgcagc tgctgcagcc gggtgccgaa ctggttaaac cgggtgccag cgtgaaactg        60
agctgcaaag cgagcggcta aacttcaac gactattggc ttaactgggt gaaacagcgt       120
ccgggccagg gcctggaatg gattggcaat gcctatccgg ctggggcat cattaactat        180 aacgaaaaat tcaaaagcaa agtgaccctg accgtggata ccagcagcag caccgtgtat       240
atgcagctgt ctagcctgac cagcgatgat agcgcggtgt attattgcgc gcgtgattat       300
gataacgcgt attggggtca gggcaccacg gtcaccgtct cctca                      345

<210> SEQ ID NO 11
<211> LENGTH: 214
<212> TYPE: PRT
<213> ORGANISM: Artificial Sequence
<220> FEATURE:
<223> OTHER INFORMATION: Synthetic

<400> SEQUENCE: 11

Asn Ile Val Met Thr Gln Ser Pro Lys Ser Met Ser Met Ser Val Gly
1               5                   10                  15

Glu Arg Val Thr Leu Thr Cys Lys Ala Ser Glu Asn Ala Gly Thr Tyr
                20                  25                  30

Val Ala Trp Tyr Gln Gln Lys Pro Glu Gln Ser Pro Lys Leu Leu Ile
            35                  40                  45

Tyr Asn Gly Ser His Arg Tyr Asp Gly Val Pro Asp Arg Phe Thr Gly
        50                  55                  60

Ser Gly Ser Ala Thr Asp Phe Thr Leu Thr Ile Ser Ser Val Gln Ala
65                  70                  75                  80

Glu Asp Leu Ala Asp Tyr Tyr Cys Gly Gln Ser Tyr Ser Tyr Pro Trp
                85                  90                  95

Thr Phe Gly Gly Gly Thr Lys Leu Glu Met Lys Arg Ala Asp Ala Ala
                100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
        130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190
```

```
Thr Cys Glu Ala Thr His Lys Thr Ser Thr Ser Pro Ile Val Lys Ser
        195                 200                 205

Phe Asn Arg Asn Glu Cys
    210

<210> SEQ ID NO 12
<211> LENGTH: 642
<212> TYPE: DNA
<213> ORGANISM: Artificial Sequence
<220> FEATURE:
<223> OTHER INFORMATION: Synthetic

<400> SEQUENCE: 12
aacattgtga tgacccagag cccgaaaagc atgagcatga gcgtgggcga acgtgtgacc      60
ctgacctgca aagcgagcga gaacgctggc acctatgttg cgtggtatca gcagaaaccg     120
gaacagtctc cgaaactgct gatctataat gggagccacc ggtatgacgg cgtgccggat     180
cgttttaccg gcagcggcag cgcgaccgat ttcaccctga ccattagcag cgtgcaggcg     240
gaagatctgg cggattatta ctgcggccag agctatagct atccgtggac ctttggcggt     300
gggaccaagc tggaaatgaa acgggctgat gcggcgccaa ctgtatccat cttcccacca     360
tccagtgagc agttaacatc tggaggtgcc tcagtcgtgt gcttcttgaa caacttctac     420
cccaaagaca tcaatgtcaa gtggaagatt gatggcagtg aacgacaaaa tggcgtcctg     480
aacagttgga ctgatcagga cagcaaagac agcacctaca gcatgagcag cacccctcacg    540 ttgaccaagg acgagtatga acgacataac agctatacct gtgaggccac tcacaagaca     600
tcaacttcac ccattgtcaa gagcttcaac aggaatgagt gt                        642

<210> SEQ ID NO 13
<211> LENGTH: 439
<212> TYPE: PRT
<213> ORGANISM: Artificial Sequence
<220> FEATURE:
<223> OTHER INFORMATION: Synthetic

<400> SEQUENCE: 13

Gln Val Gln Leu Leu Gln Pro Gly Ala Glu Leu Val Lys Pro Gly Ala
1               5                   10                  15

Ser Val Lys Leu Ser Cys Lys Ala Ser Gly Tyr Asn Phe Asn Asp Tyr
            20                  25                  30

Trp Leu Asn Trp Val Lys Gln Arg Pro Gly Gln Gly Leu Glu Trp Ile
        35                  40                  45

Gly Asn Ala Tyr Pro Gly Trp Gly Ile Ile Asn Tyr Asn Glu Lys Phe
    50                  55                  60

Lys Ser Lys Val Thr Leu Thr Val Asp Thr Ser Ser Ser Thr Val Tyr
65                  70                  75                  80

Met Gln Leu Ser Ser Leu Thr Ser Asp Asp Ser Ala Val Tyr Tyr Cys
                85                  90                  95

Ala Arg Asp Tyr Asp Asn Ala Tyr Trp Gly Gln Gly Thr Thr Val Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
    130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
```

```
            165                 170                 175
Tyr Thr Leu Ser Ser Ser Val Thr Val Pro Ser Ser Thr Trp Pro Ser
        180                 185                 190

Glu Thr Val Thr Cys Asn Val Ala His Pro Ala Ser Ser Thr Lys Val
        195                 200                 205

Asp Lys Lys Ile Val Pro Arg Asp Cys Gly Cys Lys Pro Cys Ile Cys
        210                 215                 220

Thr Val Pro Glu Val Ser Ser Val Phe Ile Phe Pro Pro Lys Pro Lys
225                 230                 235                 240

Asp Val Leu Thr Ile Thr Leu Thr Pro Lys Val Thr Cys Val Val Val
                245                 250                 255

Asp Ile Ser Lys Asp Asp Pro Glu Val Gln Phe Ser Trp Phe Val Asp
                260                 265                 270

Asp Val Glu Val His Thr Ala Gln Thr Gln Pro Arg Glu Glu Gln Phe
            275                 280                 285

Asn Ser Thr Phe Arg Ser Val Ser Glu Leu Pro Ile Met His Gln Asp
        290                 295                 300

Trp Leu Asn Gly Lys Glu Phe Lys Cys Arg Val Asn Ser Ala Ala Phe
305                 310                 315                 320

Pro Ala Pro Ile Glu Lys Thr Ile Ser Lys Thr Lys Gly Arg Pro Lys
                325                 330                 335

Ala Pro Gln Val Tyr Thr Ile Pro Pro Pro Lys Glu Gln Met Ala Lys
            340                 345                 350

Asp Lys Val Ser Leu Thr Cys Met Ile Thr Asp Phe Phe Pro Glu Asp
        355                 360                 365

Ile Thr Val Glu Trp Gln Trp Asn Gly Gln Pro Ala Glu Asn Tyr Lys
        370                 375                 380

Asn Thr Gln Pro Ile Met Asp Thr Asp Gly Ser Tyr Phe Val Tyr Ser
385                 390                 395                 400

Lys Leu Asn Val Gln Lys Ser Asn Trp Glu Ala Gly Asn Thr Phe Thr
                405                 410                 415

Cys Ser Val Leu His Glu Gly Leu His Asn His His Thr Glu Lys Ser
            420                 425                 430

Leu Ser His Ser Pro Gly Lys
        435

<210> SEQ ID NO 14
<211> LENGTH: 1317
<212> TYPE: DNA
<213> ORGANISM: Artificial Sequence
<220> FEATURE:
<223> OTHER INFORMATION: Synthetic

<400> SEQUENCE: 14
caggtgcagc tgctgcagcc gggtgccgaa ctggttaaac cgggtgccag cgtgaaactg      60
agctgcaaag cgagcggcta taacttcaac gactattggc ttaactgggt gaaacagcgt     120
ccgggccagg gcctggaatg gattggcaat gcctatccgg ctggggcat cattaactat      180 aacgaaaaat tcaaaagcaa agtgaccctg accgtggata ccagcagcag caccgtgtat     240
atgcagctgt ctagcctgac cagcgatgat agcgcggtgt attattgcgc gcgtgattat     300
gataacgcgt attggggtca gggcaccacg gtcaccgtct cctcagccaa aacgacaccc     360
ccatctgtct atccgctagc ccctggatct gccgcccaga ccaacagcat ggtgaccctg     420
ggctgtctgg tgaagggcta cttccctgag cctgtgacag tgacctggaa cagcggctct     480
```

```
ctgtctagcg gcgtgcacac attccctgcc gtgctgcaga gcgacctgta cacccctgagc    540 agcagcgtga ccgtgcctag cagcacatgg cctagcgaga ccgtgacatg caacgtggcc    600
caccctgcct cttctaccaa ggtggacaag aagatcgtgc ccagagactg cggctgcaag    660
ccttgcatct gcaccgtgcc tgaggtgagc agcgtgttca tcttcccacc caagcccaag    720
gacgtgctca ccatcaccct caccccaag gtcacgtgtg ttgtggtaga catcagcaag    780
gatgatcccg aggtccagtt cagctggttt gtagatgatg tggaggtgca cacagctcag    840
acgcaacccc gggaggagca gttcaacagc actttccgct cagtcagtga acttcccatc    900
atgcaccagg actggctcaa tggcaaggag ttcaaatgca gggtcaacag tgcagctttc    960
cctgccccca tcgagaaaac catctccaaa accaaaggca gaccgaaggc tccacaggtg   1020
tacaccattc cacctcccaa ggagcagatg gccaaggata agtcagtct gacctgcatg   1080 ataacagact tcttccctga agacattact gtggagtggc agtggaatgg gcagccagcg   1140
gagaactaca agaacactca gcccatcatg gacacagatg gctcttactt cgtctacagc   1200
aagctcaatg tgcagaagag caactgggag gcaggaaata ctttcacctg ctctgtgtta   1260
catgagggcc tgcacaacca ccatactgag aagagcctct cccactctcc tggtaaa     1317

<210> SEQ ID NO 15
<211> LENGTH: 16
<212> TYPE: PRT
<213> ORGANISM: Artificial Sequence
<220> FEATURE:
<223> OTHER INFORMATION: Synthetic

<400> SEQUENCE: 15

Arg Ser Pro Lys Ser Leu Val Gly Pro Met Gly Arg Thr Tyr Leu Tyr
1               5                   10                  15

<210> SEQ ID NO 16
<211> LENGTH: 7
<212> TYPE: PRT
<213> ORGANISM: Artificial Sequence
<220> FEATURE:
<223> OTHER INFORMATION: Synthetic

<400> SEQUENCE: 16

Arg Arg Asn Asn Leu Ala Pro
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Met Gln His Leu Glu Phe Pro Leu Thr
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Gly Tyr Asn Phe Thr Asp Tyr Trp Ile His
1               5                   10
```

-continued

<210> SEQ ID NO 19
<211> LENGTH: 17
<212> TYPE: PRT
<213> ORGANISM: Artificial Sequence
<220> FEATURE:
<223> OTHER INFORMATION: Synthetic

<400> SEQUENCE: 19

Tyr Phe Ser Thr His Ser Asp Tyr Ala Ile Ile Asn Gln Lys Phe Arg
1               5                   10                  15
Asp

<210> SEQ ID NO 20
<211> LENGTH: 7
<212> TYPE: PRT
<213> ORGANISM: Artificial Sequence
<220> FEATURE:
<223> OTHER INFORMATION: Synthetic

<400> SEQUENCE: 20

Gly Gly Leu Gly Leu Ser Tyr
1               5

<210> SEQ ID NO 21
<211> LENGTH: 113
<212> TYPE: PRT
<213> ORGANISM: Artificial Sequence
<220> FEATURE:
<223> OTHER INFORMATION: Synthetic

<400> SEQUENCE: 21

Asp Ile Val Met Thr Gln Ala Ala Pro Ser Val Leu Val Thr Pro Gly
1               5                   10                  15

Glu Ser Val Ser Ile Ser Cys Arg Ser Pro Lys Ser Leu Val Gly Pro
            20                  25                  30

Met Gly Arg Thr Tyr Leu Tyr Trp Phe Leu Gln Arg Pro Gly Gln Ser
        35                  40                  45

Pro Gln Leu Leu Ile Tyr Arg Arg Asn Asn Leu Ala Pro Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Ile Tyr Tyr Cys Met Gln His
                85                  90                  95

Leu Glu Phe Pro Leu Thr Phe Gly Ala Gly Thr Lys Leu Glu Ile Lys
            100                 105                 110

Arg

<210> SEQ ID NO 22
<211> LENGTH: 339
<212> TYPE: DNA
<213> ORGANISM: Artificial Sequence
<220> FEATURE:
<223> OTHER INFORMATION: Synthetic

<400> SEQUENCE: 22
gatattgtga tgacccaggc agcgccgagc gttctggtta ccccgggtga aagcgtgagc      60
attagctgcc gaagcccaaa aagcctagtg ggtcccatgg gaaggaccta tctatattgg     120
tttctgcagc gtccgggtca gagccgcag ctgctgattt atcgtcggaa caacctggca     180
ccaggtgtgc cggatcgttt tagcggcagc ggtagcggca ccgcgtttac cctgcgtatt     240

```
agccgtgtgg aagcggaaga tgtgggcatt tattattgca tgcagcacct ggaattcccg    300
ctgacctttg gtgcgggcac caagctggaa atcaaacgg                           339
```

<210> SEQ ID NO 23
<211> LENGTH: 116
<212> TYPE: PRT
<213> ORGANISM: Artificial Sequence
<220> FEATURE:
<223> OTHER INFORMATION: Synthetic

<400> SEQUENCE: 23

```
Gln Val Gln Leu Gln Gln Ser Gly Ala Glu Leu Val Lys Pro Gly Ala
1               5                   10                  15

Ser Val Lys Met Ser Cys Lys Ala Ser Gly Tyr Asn Phe Thr Asp Tyr
            20                  25                  30

Trp Ile His Trp Val Lys Glu Arg Pro Gly Gln Gly Leu Glu Trp Ile
        35                  40                  45

Gly Tyr Phe Ser Thr His Ser Asp Tyr Ala Ile Ile Asn Gln Lys Phe
    50                  55                  60

Arg Asp Lys Ala Thr Leu Thr Ala Asp Lys Ser Ser Arg Leu Ala Tyr
65                  70                  75                  80

Met Gln Leu Ser Ser Leu Thr Ser Glu Asp Ser Ala Ile Tyr Tyr Cys
                85                  90                  95

Ala Arg Gly Gly Leu Gly Leu Ser Tyr Trp Gly Gln Gly Thr Thr Val
            100                 105                 110

Thr Val Ser Ser
        115
```

<210> SEQ ID NO 24
<211> LENGTH: 348
<212> TYPE: DNA
<213> ORGANISM: Artificial Sequence
<220> FEATURE:
<223> OTHER INFORMATION: Synthetic

<400> SEQUENCE: 24

```
caggtgcagc tgcagcagag cggtgcggaa ctggtgaaac cgggtgcgag cgtgaaaatg    60
agctgcaaag cgagcggcta taactttaca gattattgga ttcactgggt gaaagaacgt   120
ccgggccagg gcctggaatg gattggctat tttagtacgc atagcgatta tgccatcatt   180
aaccagaaat tcagagataa agcgaccctg accgcggata aaagcagccg tctggcctat   240
atgcagctgt ctagcctgac cagcgaagat agcgcgattt attactgcgc gcgtggcggc   300
ttaggcctga gctattgggg ccagggtacc acggtcacag tctcctca              348
```

<210> SEQ ID NO 25
<211> LENGTH: 219
<212> TYPE: PRT
<213> ORGANISM: Artificial Sequence
<220> FEATURE:
<223> OTHER INFORMATION: Synthetic

<400> SEQUENCE: 25

```
Asp Ile Val Met Thr Gln Ala Ala Pro Ser Val Leu Thr Pro Gly
1               5                   10                  15

Glu Ser Val Ser Ile Ser Cys Arg Ser Pro Lys Ser Leu Val Gly Pro
            20                  25                  30

Met Gly Arg Thr Tyr Leu Tyr Trp Phe Leu Gln Arg Pro Gly Gln Ser
        35                  40                  45
```

Pro Gln Leu Leu Ile Tyr Arg Arg Asn Asn Leu Ala Pro Gly Val Pro
        50                  55                  60

Asp Arg Phe Ser Gly Ser Gly Ser Gly Thr Ala Phe Thr Leu Arg Ile
 65              70                  75                  80

Ser Arg Val Glu Ala Glu Asp Val Gly Ile Tyr Tyr Cys Met Gln His
                 85                  90                  95

Leu Glu Phe Pro Leu Thr Phe Gly Ala Gly Thr Lys Leu Glu Ile Lys
            100                 105                 110

Arg Ala Asp Ala Ala Pro Thr Val Ser Ile Phe Pro Pro Ser Ser Glu
            115                 120                 125

Gln Leu Thr Ser Gly Gly Ala Ser Val Val Cys Phe Leu Asn Asn Phe
        130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 26
<211> LENGTH: 657
<212> TYPE: DNA
<213> ORGANISM: Artificial Sequence
<220> FEATURE:
<223> OTHER INFORMATION: Synthetic

<400> SEQUENCE: 26
gatattgtga tgacccaggc agcgccgagc gttctggtta ccccgggtga aagcgtgagc      60
attagctgcc gaagcccaaa aagcctagtg ggtcccatgg aaggaccta tctatattgg     120 tttctgcagc gtccgggtca gagcccgcag ctgctgattt atcgtcggaa caacctggca     180
ccaggtgtgc cggatcgttt tagcggcagc ggtagcggca ccgcgtttac cctgcgtatt     240
agccgtgtgg aagcggaaga tgtgggcatt tattattgca tgcagcacct ggaattcccg     300
ctgacctttg gtgcgggcac caagctggaa atcaaacggg ctgatgcggc gcccactgta     360
tccatcttcc caccatccag tgagcagtta acatctggag gtgctagcgt cgtgtgcttc     420
ttgaacaact ctaccccaa agacatcaat gtcaagtgga gattgatgg cagtgaacga     480 caaaatggcg tcctgaacag ttggactgat caggacagca agacagcac ctacagcatg     540 agcagcaccc tcacgttgac caaggacgag tatgaacgac ataacagcta cctgtgag     600 gccactcaca gacatcaac ttcacccatt gtcaagagct caacaggaa tgagtgt          657

<210> SEQ ID NO 27
<211> LENGTH: 440
<212> TYPE: PRT
<213> ORGANISM: Artificial Sequence
<220> FEATURE:
<223> OTHER INFORMATION: Synthetic

<400> SEQUENCE: 27

Gln Val Gln Leu Gln Gln Ser Gly Ala Glu Leu Val Lys Pro Gly Ala
 1               5                  10                  15

```
Ser Val Lys Met Ser Cys Lys Ala Ser Gly Tyr Asn Phe Thr Asp Tyr
            20                  25                  30

Trp Ile His Trp Val Lys Glu Arg Pro Gly Gln Gly Leu Glu Trp Ile
        35                  40                  45

Gly Tyr Phe Ser Thr His Ser Asp Tyr Ala Ile Ile Asn Gln Lys Phe
    50                  55                  60

Arg Asp Lys Ala Thr Leu Thr Ala Asp Lys Ser Ser Arg Leu Ala Tyr
65                  70                  75                  80

Met Gln Leu Ser Ser Leu Thr Ser Glu Asp Ser Ala Ile Tyr Tyr Cys
                85                  90                  95

Ala Arg Gly Gly Leu Gly Leu Ser Tyr Trp Gly Gln Gly Thr Thr Val
            100                 105                 110

Thr Val Ser Ser Ala Lys Thr Thr Pro Pro Ser Val Tyr Pro Leu Ala
        115                 120                 125

Pro Gly Ser Ala Ala Gln Thr Asn Ser Met Val Thr Leu Gly Cys Leu
    130                 135                 140

Val Lys Gly Tyr Phe Pro Glu Pro Val Thr Val Thr Trp Asn Ser Gly
145                 150                 155                 160

Ser Leu Ser Ser Gly Val His Thr Phe Pro Ala Val Leu Gln Ser Asp
                165                 170                 175

Leu Tyr Thr Leu Ser Ser Val Thr Val Pro Ser Ser Thr Trp Pro
            180                 185                 190

Ser Glu Thr Val Thr Cys Asn Val Ala His Pro Ala Ser Ser Thr Lys
                195                 200                 205

Val Asp Lys Lys Ile Val Pro Arg Asp Cys Gly Cys Lys Pro Cys Ile
    210                 215                 220

Cys Thr Val Pro Glu Val Ser Ser Val Phe Ile Phe Pro Pro Lys Pro
225                 230                 235                 240

Lys Asp Val Leu Thr Ile Thr Leu Thr Pro Lys Val Thr Cys Val Val
            245                 250                 255

Val Asp Ile Ser Lys Asp Asp Pro Glu Val Gln Phe Ser Trp Phe Val
        260                 265                 270

Asp Asp Val Glu Val His Thr Ala Gln Thr Gln Pro Arg Glu Glu Gln
    275                 280                 285

Phe Asn Ser Thr Phe Arg Ser Val Ser Glu Leu Pro Ile Met His Gln
    290                 295                 300

Asp Trp Leu Asn Gly Lys Glu Phe Lys Cys Arg Val Asn Ser Ala Ala
305                 310                 315                 320

Phe Pro Ala Pro Ile Glu Lys Thr Ile Ser Lys Thr Lys Gly Arg Pro
            325                 330                 335

Lys Ala Pro Gln Val Tyr Thr Ile Pro Pro Lys Glu Gln Met Ala
        340                 345                 350

Lys Asp Lys Val Ser Leu Thr Cys Met Ile Thr Asp Phe Phe Pro Glu
    355                 360                 365

Asp Ile Thr Val Glu Trp Gln Trp Asn Gly Gln Pro Ala Glu Asn Tyr
    370                 375                 380

Lys Asn Thr Gln Pro Ile Met Asp Thr Asp Gly Ser Tyr Phe Val Tyr
385                 390                 395                 400

Ser Lys Leu Asn Val Gln Lys Ser Asn Trp Glu Ala Gly Asn Thr Phe
            405                 410                 415
```

Thr Cys Ser Val Leu His Glu Gly Leu His Asn His Thr Glu Lys
            420                 425                 430

Ser Leu Ser His Ser Pro Gly Lys
        435                 440

<210> SEQ ID NO 28
<211> LENGTH: 1320
<212> TYPE: DNA
<213> ORGANISM: Artificial Sequence
<220> FEATURE:
<223> OTHER INFORMATION: Synthetic

<400> SEQUENCE: 28

```
caggtgcagc tgcagcagag cggtgcggaa ctggtgaaac cgggtgcgag cgtgaaaatg      60
agctgcaaag cgagcggcta aactttaca gattattgga ttcactgggt gaaagaacgt     120
ccgggccagg gcctggaatg gattggctat tttagtacgc atagcgatta tgccatcatt     180
aaccagaaat tcagagataa agcgaccctg accgcggata aaagcagccg tctggcctat     240
atgcagctgt ctagcctgac cagcgaagat agcgcgattt attactgcgc gcgtggcggc     300
ttaggcctga gctattgggg ccagggtacc acggtcacag tctcctcagc caaaacgaca     360
cccccatctg tctatccgct agccctggga tctgccgccc agaccaacag catggtgacc     420
ctgggctgtc tggtgaaggg ctacttccct gagcctgtga cagtgacctg aacagcggc     480
tctctgtcta cggcgtgca cacattccct gccgtgctgc agagcgacct gtacaccctg     540
agcagcagcg tgaccgtgcc tagcagcaca tggcctagcg agaccgtgac atgcaacgtg     600
gcccaccctg cctcttctac caaggtggac aagaagatcg tgcccagaga ctgcggctgc     660
aagccttgca tctgcaccgt gcctgaggtg agcagcgtgt tcatcttccc acccaagccc     720
aaggacgtgc tcaccatcac cctcaccccc aaggtcacgt gtgttgtggt agacatcagc     780
aaggatgatc ccgaggtcca gttcagctgg tttgtagatg atgtggaggt gcacacagct     840
cagacgcaac cccgggagga gcagttcaac agcactttcc gctcagtcag tgaacttccc     900
atcatgcacc aggactggct caatggcaag gagttcaaat gcagggtcaa cagtgcagct     960
ttccctgccc ccatcgagaa aaccatctcc aaaaccaaag cagaccgaa ggctccacag    1020
gtgtacacca ttccacctcc caaggagcag atggccaagg ataaagtcag tctgacctgc    1080
atgataacag acttcttccc tgaagacatt actgtggagt ggcagtggaa tgggcagcca    1140
gcggagaact acaagaacac tcagcccatc atggacacag atggctctta cttcgtctac    1200
agcaagctca atgtgcagaa gagcaactgg gaggcaggaa atactttcac ctgctctgtg    1260
ttacatgagg gcctgcacaa ccaccatact gagaagagcc tctcccactc tcctggtaaa    1320
```

<210> SEQ ID NO 29
<211> LENGTH: 29
<212> TYPE: PRT
<213> ORGANISM: Homo sapiens

<400> SEQUENCE: 29

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

ANTI-GLUCAGON ANTIBODIES AND USES THEREOF

This is the national phase application, under 35 USC 371, for PCT/US2012/066587, filed Nov. 27, 2012, which claims the benefit, under 35 USC 119(e), of U.S. provisional application 61/566,080 filed Dec. 2, 2011.

The present invention relates to the field of medicine. More particularly, the present invention relates to antibodies that bind glucagon to form a detectable glucagon/anti-glucagon monoclonal antibody complex useful in diagnostic techniques that require labeling, marking, identifying, or quantifying glucagon, such as imaging and determination of glucagon levels. The antibodies of the present invention are useful for diagnostic applications that aid in identifying patients with conditions resulting in altered levels of glucagon, as well as monitoring and/or improving the treatment of patients with glucagon receptor antagonists or other therapeutics.

Glucagon is a 29-residue polypeptide hormone that is produced in the pancreas by the α-cells of the islets of Langerhans, and the amino acid sequence of the peptide is completely conserved in mammals. Glucagon and glucagon-like peptides are transcribed from a common proglucagon gene that is expressed in the pancreas, intestine, and brain. Basal amounts of glucagon are essential for the maintenance of normoglycemia, and a key physiological role of glucagon is to prevent hypoglycemia. Glucagon levels increase rapidly in response to hypoglycemia, and the glucagon response is the primary defense mechanism utilized by the body to restore blood glucose to normal levels.

A complex interplay of signaling factors are required for the proper regulation of glucagon secretion. These controlling factors, which include glucose, intra-islet paracrine factors such as insulin and GLP-1, and the central and autonomic nervous systems, interact in a coordinated fashion to regulate glucagon secretion. The glucagon receptor is predominantly expressed in the liver where its activation leads to increased glucose production. Glucagon receptors are also expressed at lower levels in many other tissues.

Glucagon has been considered to be a critical factor in the pathology of diabetes. It has been proposed that improper expression of glucagon may contribute to the development of the hyperglycemia in diabetes. Recent studies have also implicated glucagon as an important component in the process of regulation of energy metabolism. Given the importance of glucagon in glucose homeostasis and diabetes, glucagon has been considered an important biomarker related to diabetes and development of anti-diabetic therapies (R. Krishna, G. Herman, and J. A. Wagner., Accelerating Drug Development Using Biomarkers: A Case Study with Sitagliptin, A Novel DPP4 Inhibitor for Type 2 Diabetes, AAPS Journal, Vol. 10, No. 2, p401-409, June 2008).

Due to the role of glucagon signaling in regulating normoglycemia, and the disease states that arise from failure to maintain normoglycemia, the glucagon signaling pathway is considered to be an attractive target for anti-diabetic therapy. For example, recently study results from glucagon receptor antagonists have described significant reductions in blood glucose and hemoglobin A1c levels in diabetic patients. However, glucagon receptor antagonists are also reported to elevate glucagon levels, and therefore sensitive and accurate technology to determine glucagon levels is needed for both the analysis of glucagon levels in diabetic patients, and the development of glucagon receptor antagonists and/or other therapeutics.

Methods of detecting glucagon are known in the art, however these methods lack the particular combination of desirable properties and advantages found in the present invention. A radioimmunoassay to measure glucagon was first described fifty years ago. Since that time, there have been advances in immunoassay methods, such as those described in Guillo et al., which recites a capillary electrophoresis competitive immunoassay for the simultaneous quantitation of insulin, glucagon, and islet amyloid polypeptide (IAPP) secretion from islets of Langerhans (Simultaneous capillary electrophoresis competitive immunoassay for insulin, glucagon, and islet amyloid polypeptide secretion from mouse islets of Langerhans. Journal of Chromatography, Guillo C. Roper M G., 1218(26):4059-64, July 2011). However, the methods of Guillo and Roper employ the monoclonal antibody K79bB10, which is commercially available from Sigma-Aldrich (Product No. G 2654), and is reported to bind to glucagon with an affinity constant of $6.1 \times 10^8$ $M^{-1}$ in radioimmunoassays (See the product insert for Product No. G 2654, and Witt, S., et al., Acta Histochem., Suppl XXXV, 217 (1988)).

In view of the important role of glucagon in diabetic patients, there exists a need for diagnostic antibody technology with an improved combination of desirable properties, including specificity, affinity, and sensitivity, to detect and/or quantitate biological glucagon levels to identify and monitor changes in glucagon levels, and improve therapeutic interventions in view of these changes. For example, technology is needed to determine if treatment with one or more glucagon receptor antagonists, or other therapeutic agents, has resulted in a changed glucagon level in a patient.

In particular, there is a need for anti-glucagon antibodies that are specific for glucagon and possess improved binding affinity. More particularly there is a need for anti-glucagon antibodies that are specific for glucagon, and possess improved binding affinity, and demonstrate enhanced sensitivity in glucagon determinations. Even more particularly there is a need for anti-glucagon antibodies that are specific for glucagon, and possess improved binding affinity, and demonstrate enhanced sensitivity in glucagon determinations, and improved ELISA assay conditions that result in minimal interference and broad dilutional linearity. Preferably the antibodies are monoclonal antibodies, and include two distinct antibodies that recognize two distinct epitopes on glucagon.

The antibodies of the present invention are found to possess surprisingly improved affinity for glucagon as compared to K79bB10. Binding of glucagon with an anti-glucagon antibody of the present invention permits diagnostic assessment of glucagon levels, before, during, and/or after treatment of the patient, with minimal plasma protein interference and with improved sensitivity. Accordingly, the present invention provides alternative anti-glucagon antibodies that specifically bind to independent epitopes of glucagon, including one that binds the C-terminus of glucagon. The present invention further provides a highly specific electrochemiluminescent (ECL) sandwich immunoassay with superior sensitivity, recovery, and dilutional linearity which provides a rapid and convenient method for quantifying glucagon in high throughput formats.

One aspect of the present invention pertains to a monoclonal antibody, or antigen-binding fragment thereof, that specifically binds to glucagon consisting of the amino acid sequence as in SEQ ID NO: 29, said antibody, or antigen-binding fragment thereof, comprising:

light chain complementarity determining regions LCDR1, LCDR2, and LCDR3 comprising the amino acid sequences KASENAGTYVA (SEQ ID NO: 1), NGSHRYD (SEQ ID NO: 2), and GQSYSYPWT (SEQ ID NO: 3), respectively, and heavy chain complementarity determining regions HCDR1, HCDR2, and HCDR3 comprising the amino acid sequences GYNFNDYWLN (SEQ ID NO: 4), NAYPG-WGIINYNEKFKS (SEQ ID NO: 5), and DYDNAY (SEQ ID NO: 6), respectively.

Another embodiment of the present invention is a monoclonal antibody, or antigen-binding fragment thereof, that specifically binds to glucagon consisting of the amino acid sequence as in SEQ ID NO: 29, said monoclonal antibody comprising:

a light chain variable region (LCVR) comprising the amino acid sequence as in SEQ ID NO: 7, and a heavy chain variable region (HCVR) comprising the amino acid sequence as in SEQ ID NO: 9.

In another embodiment, the present invention provides a monoclonal antibody, or antigen-binding fragment thereof, that specifically binds to glucagon consisting of the amino acid sequence as in SEQ ID NO: 29, said monoclonal antibody comprising:

a light chain comprising the amino acid sequence as in SEQ ID NO: 11, and a heavy chain comprising the amino acid sequence as in SEQ ID NO: 13.

Another aspect of the present invention pertains to a monoclonal antibody, or antigen-binding fragment thereof, that specifically binds to glucagon consisting of the amino acid sequence as in SEQ ID NO: 29, said antibody, or antigen-binding fragment thereof, comprising:

light chain complementarity determining regions LCDR1, LCDR2, and LCDR3 comprising the amino acid sequences RSPKSLVGPMGRTYLY (SEQ ID NO: 15), RRNNLAP (SEQ ID NO: 16), and MQHLEFPLT (SEQ ID NO: 17), respectively, and heavy chain complementarity determining regions HCDR1, HCDR2, and HCDR3 comprising the amino acid sequences GYNFTDYWIH (SEQ ID NO: 18), YFSTHS-DYAIINQKFRD (SEQ ID NO: 19), and GGLGLSY (SEQ ID NO: 20), respectively.

Another aspect of the present invention pertains to a monoclonal antibody, or antigen-binding fragment thereof, that specifically binds to glucagon consisting of the amino acid sequence as in SEQ ID NO: 29, said antibody, or antigen-binding fragment thereof, comprising:

light chain complementarity determining regions LCDR1, LCDR2, and LCDR3 wherein the amino acid sequences are RSPKSLVGPMGRTYLY (SEQ ID NO: 15), RRNNLAP (SEQ ID NO: 16), and MQHLEFPLT (SEQ ID NO: 17), respectively, and heavy chain complementarity determining regions HCDR1, HCDR2, and HCDR3 wherein the amino acid sequences are GYNFTDYWIH (SEQ ID NO: 18), YFSTHSDYAIINQKFRD (SEQ ID NO: 19), and GGL-GLSY (SEQ ID NO: 20), respectively.

Another embodiment of the present invention is a monoclonal antibody, or antigen-binding fragment thereof, that specifically binds to glucagon consisting of the amino acid sequence as in SEQ ID NO: 29, said monoclonal antibody comprising:

a light chain variable region (LCVR) comprising the amino acid sequence as in SEQ ID NO: 21, and a heavy chain variable region (HCVR) comprising the amino acid sequence as in SEQ ID NO: 23.

In another embodiment, the present invention provides a monoclonal antibody, or antigen-binding fragment thereof, that specifically binds to glucagon consisting of the amino acid sequence as in SEQ ID NO: 29, said monoclonal antibody comprising:

a light chain comprising the amino acid sequence as in SEQ ID NO: 25, and a heavy chain comprising the amino acid sequence as in SEQ ID NO: 27.

A preferred embodiment of the present invention is an antibody referred to herein as IBA009 which comprises two heavy chains of (SEQ ID NO: 13) and two light chains of (SEQ ID NO: 11). A more preferred embodiment of the present invention is an antibody referred to herein as IBA032 which comprises two heavy chains of (SEQ ID NO: 27) and two light chains of (SEQ ID NO: 25).

Another embodiment of the present invention provides a diagnostically useful composition comprising at least one of the foregoing anti-glucagon monoclonal antibodies, or antigen-binding fragments thereof, of the present invention and a diagnostically acceptable carrier, diluent, or excipient. In one such embodiment, an anti-glucagon monoclonal antibody, or antigen-binding fragment thereof, of the present invention is covalently, non-covalently, or partially covalently and partially non-covalently linked to a label.

In another embodiment, the present invention encompasses a composition comprising at least one of the foregoing anti-glucagon monoclonal antibodies, or antigen-binding fragments thereof, of the present invention bound to a polypeptide comprising the glucagon amino acid sequence as in SEQ ID NO: 29. Preferably, an anti-glucagon monoclonal antibody, or antigen-binding fragment thereof, of the present invention is bound to a polypeptide comprising the glucagon amino acid sequence as in SEQ ID NO: 29 at an epitope which includes the c-terminus of SEQ ID NO: 29. More preferably, the present invention encompasses a composition comprising at least one of the foregoing anti-glucagon monoclonal antibodies, or antigen-binding fragments thereof, of the present invention bound to a polypeptide comprising the glucagon amino acid sequence as in SEQ ID NO: 29 and further comprises a diagnostically acceptable carrier, diluent, or excipient.

In other embodiments, the present invention provides a kit, comprising a container comprising a monoclonal antibody, or antigen-binding fragment thereof, that specifically binds to a polypeptide comprising the glucagon amino acid sequence as in SEQ ID NO: 29, said monoclonal antibody, or antigen-binding fragment thereof, comprising:

light chain complementarity determining regions LCDR1, LCDR2, and LCDR3 comprising the amino acid sequences RSPKSLVGPMGRTYLY (SEQ ID NO: 15), RRNNLAP (SEQ ID NO: 16), and MQHLEFPLT (SEQ ID NO: 17), respectively, and heavy chain complementarity determining regions HCDR1, HCDR2, and HCDR3 comprising the amino acid sequences GYNFTDYWIH (SEQ ID NO: 18), YFSTHS-DYAIINQKFRD (SEQ ID NO: 19), and GGLGLSY (SEQ ID NO: 20), respectively.

In other embodiments, the present invention provides a kit, comprising a container comprising a first monoclonal antibody, or antigen-binding fragment thereof, that specifically binds to a polypeptide comprising the glucagon amino acid sequence as in SEQ ID NO: 29, said monoclonal antibody, or antigen-binding fragment thereof, comprising:

light chain complementarity determining regions LCDR1, LCDR2, and LCDR3 comprising the amino acid sequences RSPKSLVGPMGRTYLY (SEQ ID NO: 15), RRNNLAP (SEQ ID NO: 16), and MQHLEFPLT (SEQ ID NO: 17), respectively, and heavy chain complementarity determining regions HCDR1, HCDR2, and HCDR3 comprising the amino acid sequences GYNFTDYWIH (SEQ ID NO: 18), YFSTHS-DYAIINQKFRD (SEQ ID NO: 19), and GGLGLSY (SEQ ID NO: 20), respectively;

and a container comprising a second monoclonal antibody, or antigen-binding fragment thereof, that specifically binds to a polypeptide comprising the glucagon amino acid sequence as in SEQ ID NO: 29, said monoclonal antibody, or antigen-binding fragment thereof, comprising:

light chain complementarity determining regions LCDR1, LCDR2, and LCDR3 comprising the amino acid sequences KASENAGTYVA (SEQ ID NO: 1), NGSHRYD (SEQ ID NO: 2), and GQSYSYPWT (SEQ ID NO: 3), respectively, and heavy chain complementarity determining regions HCDR1, HCDR2, and HCDR3 comprising the amino acid sequences GYNFNDYWLN (SEQ ID NO: 4), NAYPG-WGIINYNEKFKS (SEQ ID NO: 5), and DYDNAY (SEQ ID NO: 6), respectively.

In certain embodiments, the kit may comprise a second container comprising a secondary antibody that binds to the monoclonal antibody of the invention, or antigen-binding fragment thereof, and, optionally, instructions for using the monoclonal antibody, or antigen-binding fragment thereof, with or without the secondary antibody, to detect glucagon in vivo, ex vivo or in vitro. In some embodiments, the secondary antibody can be conjugated to an enzyme known to be used in immunoassays. In other embodiments, the kit can further comprise another container comprising a chromogenic substrate of the aforementioned enzyme.

In other embodiments, the present invention also encompasses a method of detecting glucagon expressed by a mammalian cell comprising:

(a) contacting a cell with a detectably labeled monoclonal antibody, or antigen-binding fragment thereof, that specifically binds to glucagon consisting of the amino acid sequence as in SEQ ID NO: 29, said monoclonal antibody, or antigen-binding fragment thereof, comprising:

light chain complementarity determining regions LCDR1, LCDR2, and LCDR3 comprising the amino acid sequences RSPKSLVGPMGRTYLY (SEQ ID NO: 15), RRNNLAP (SEQ ID NO: 16), and MQHLEFPLT (SEQ ID NO: 17), respectively, and heavy chain complementarity determining regions HCDR1, HCDR2, and HCDR3 comprising the amino acid sequences GYNFTDYWIH (SEQ ID NO: 18), YFSTHSDYAIINQKFRD (SEQ ID NO: 19), and GGL-GLSY (SEQ ID NO: 20), respectively;

(b) optionally, removing any non-specifically bound monoclonal antibody or antigen-binding fragment thereof; and (c) detecting and/or quantifying the amount of labeled monoclonal antibody or antigen-binding fragment thereof which is specifically bound to the glucagon using any art-known method, for example, cytometric or immunohistochemical techniques. Preferably, the glucagon is detected in a biological tissue or a bodily fluid from a diabetic patient such as in urine, ascites fluid, lymphatic fluid, spinal fluid, bronchial fluid, and, more preferably, blood, serum or plasma.

The present invention also provides a method of determining the glucagon level in a bodily fluid comprising: (a) contacting the bodily fluid with an anti-glucagon diagnostic monoclonal antibody, or antigen-binding fragment thereof, that specifically binds to glucagon consisting of the amino acid sequence as in SEQ ID NO: 29, the antibody, or antigen-binding fragment thereof, comprising: light chain complementarity determining regions LCDR1, LCDR2, and LCDR3 comprising the amino acid sequences RSPK-SLVGPMGRTYLY (SEQ ID NO: 15), RRNNLAP (SEQ ID NO: 16), and MQHLEFPLT (SEQ ID NO: 17), respectively, and heavy chain complementarity determining regions HCDR1, HCDR2, and HCDR3 comprising the amino acid sequences GYNFTDYWIH (SEQ ID NO: 18), YFSTHS-DYAIINQKFRD (SEQ ID NO: 19), and GGLGLSY (SEQ ID NO: 20), respectively; (b) optionally, removing any non-specifically bound monoclonal antibody or, antigen-binding fragment thereof; and (c) detecting and/or quantifying the amount of monoclonal antibody, or antigen-binding fragment thereof, which is specifically bound to glucagon. Preferably the antibody used in this method is IBA032.

The present invention also provides a method of detecting and/or quantifying glucagon levels in a mammalian biological tissue or a bodily fluid from a diabetic patient, or patient at risk of developing diabetes, such as in urine, ascites fluid, lymphatic fluid, spinal fluid, bronchial fluid, and, preferably, blood, serum or plasma, comprising: contacting the tissue with a monoclonal antibody, or antigen-binding fragment thereof, that specifically binds to glucagon, said monoclonal antibody, or antigen-binding fragment thereof, comprising: light chain complementarity determining regions LCDR1, LCDR2, and LCDR3 comprising the amino acid sequences RSPKSLVGPMGRTYLY (SEQ ID NO: 15), RRNNLAP (SEQ ID NO: 16), and MQHLEFPLT (SEQ ID NO: 17), respectively, and heavy chain complementarity determining regions HCDR1, HCDR2, and HCDR3 comprising the amino acid sequences GYNFTDYWIH (SEQ ID NO: 18), YFSTHSDYAIINQKFRD (SEQ ID NO: 19), and GGL-GLSY (SEQ ID NO: 20), respectively, under conditions that permit formation of a detectable glucagon/anti-glucagon monoclonal antibody complex; and detecting and/or quantifying said complex(es). Preferably the antibody used in this method is IBA032. Preferably the contacting of the sample and the antibody of the invention occur ex vivo. More preferably the antibody used in this method is IBA032 and contacting of the sample and the antibody of the invention occur ex vivo.

In various embodiments, the contacting can be carried out in vivo, the anti-glucagon monoclonal antibody, or antigen-binding fragment thereof, can be administered parenterally, by injection or infusion. Additionally, in various embodiments, the anti-glucagon monoclonal antibody, or antigen-binding fragment thereof, is labeled with at least one detectable label including, but not limited to, the labels described herein, or otherwise known in the art. Detection can be performed in vitro and/or in vivo using a method, technology and/or device known in the art to be appropriate for a specific detectable label including, but not limited to, a gamma counter, a scintillation counter, by autoradiography, devices including, for example, a fluorescence measuring device, a bioluminescence measuring device, a magnetic resonance imaging (MRI) device, a magnetic device, a positron emission tomography (PET) device, a computed tomography (CT) device, an ultrasound device, an optical coherence tomography (OCT) device, and/or a single photon emission computed tomography (SPECT) device.

In another embodiment, the present invention provides the use of a kit comprising a monoclonal antibody, or antigen-binding fragment thereof, that specifically binds to glucagon (SEQ ID NO: 29), said monoclonal antibody, or antigen-binding fragment thereof, comprising:

light chain complementarity determining regions LCDR1, LCDR2, and LCDR3 comprising the amino acid sequences RSPKSLVGPMGRTYLY (SEQ ID NO: 15), RRNNLAP (SEQ ID NO: 16), and MQHLEFPLT (SEQ ID NO: 17), respectively, and heavy chain complementarity determining regions HCDR1, HCDR2, and HCDR3 comprising the amino acid sequences GYNFTDYWIH (SEQ ID NO: 18), YFSTHSDYAIINQKFRD (SEQ ID NO: 19), and GGL-GLSY (SEQ ID NO: 20), respectively, for:

(a) detecting and/or quantifying glucagon in or on a cell;
(b) detecting and/or quantifying glucagon expressing cells in a patient;
(c) detecting and/or quantifying glucagon expressing cells in a tissue sample of a patient;
(d) detecting and/or quantifying glucagon in a bodily fluid from a patient such as in blood, plasma, serum, urine, ascites fluid, lymphatic fluid, spinal fluid, and bronchial fluid;
(e) assessing whether an individual has, or is at risk for developing, diabetes wherein glucagon expression is higher or lower than in healthy control subjects;
(f) selecting a patient having a condition for treatment with a glucagon receptor antagonist;
(g) determining response to treatment with glucagon receptor antagonist; and/or
(h) treating diabetes.

Preferably, with respect to (g) and (h) above, the treatment includes the administration of a glucagon receptor antagonist such as Bay-27-9955 which is shown below as Structure 1 (Petersen, K F. Sullivan, J T., Effects of a novel glucagon receptor antagonist (Bay 27-9955), on glucagon-stimulated glucose production in humans. Diabetologia. 44(11):2018-24, 2001 November).

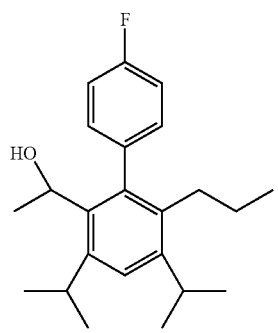

Structure 1

Thus, the anti-glucagon antibodies described herein may be useful as diagnostics to aid in identification of diabetic patients with altered levels of glucagon, or in the diagnosis of other conditions known to result in elevated levels of glucagon. Furthermore, the anti-glucagon antibodies of the present invention may be used to monitor and/or optimize a diabetic patient's treatment with glucagon signaling targeted therapeutic agents, such as Bay 27-9955, or the small molecule antagonists of the glucagon receptor described in WO 2005/123668, as well as the antibody antagonists of the glucagon receptor such as those described in WO 2009/120530.

Another aspect of the present invention provides isolated nucleic acid molecules encoding the anti-glucagon antibodies of the invention, expression vectors comprising the nucleic acid molecules, and host cells comprising the nucleic acid molecules.

DESCRIPTION OF THE FIGURES

FIG. 1A: Glucagon antibody specificity. (A) Capture antibody IBA009 Biacore analysis. Binding with 10 nM glucagon (labeled as "GCG 10 nM"), 100 nM oxyntomodulin (labeled as "Oxy 100 nM"), and buffer-only negative control (labeled as "buffer") are shown. The capture antibody IBA009 binds an internal region of glucagon and is determined to cross-react with oxyntomodulin (FIG. 1-A).

FIG. 2 shows a typical standard curve obtained with the ELISA as described in Example 3. Glucagon peptide (SEQ ID NO: 29) is used to generate a calibration curve starting at a concentration of 1950 pmol/L, with serial 1:3 dilutions (FIG. 2, curve "IBA009 capture-IBA032 Detection"). Anti-mid region antibody IBA009 is the capture antibody and anti-glucagon C-terminal antibody IBA032 is the detection antibody. As FIG. 2 illustrates, the ELISA of Example 3 has broad dynamic range, low background, and high sensitivity. The ELISA of Example 3 also demonstrates acceptable dilutional linearity down to 1:2 and up to a 1:16 dilution. For comparison, the data reported in the product insert for the commercially available Mesoscale Discovery glucagon ELISA kit (Catalog K11160C-1) is shown as "MSD KIT".

The correlation between plasma glucagon concentration is determined by the ELISA of Example 3 as well as a competitive RIA commercially available from ALPCO, Salem, N.H. Glucagon concentrations are determined for 26 samples and FIG. 3 shows the results obtained after analyzing split samples in both assays. As illustrated in FIG. 3, the glucagon values obtained in the two different assays were highly correlated (r=0.97, P<0.001).

Figure 1B:
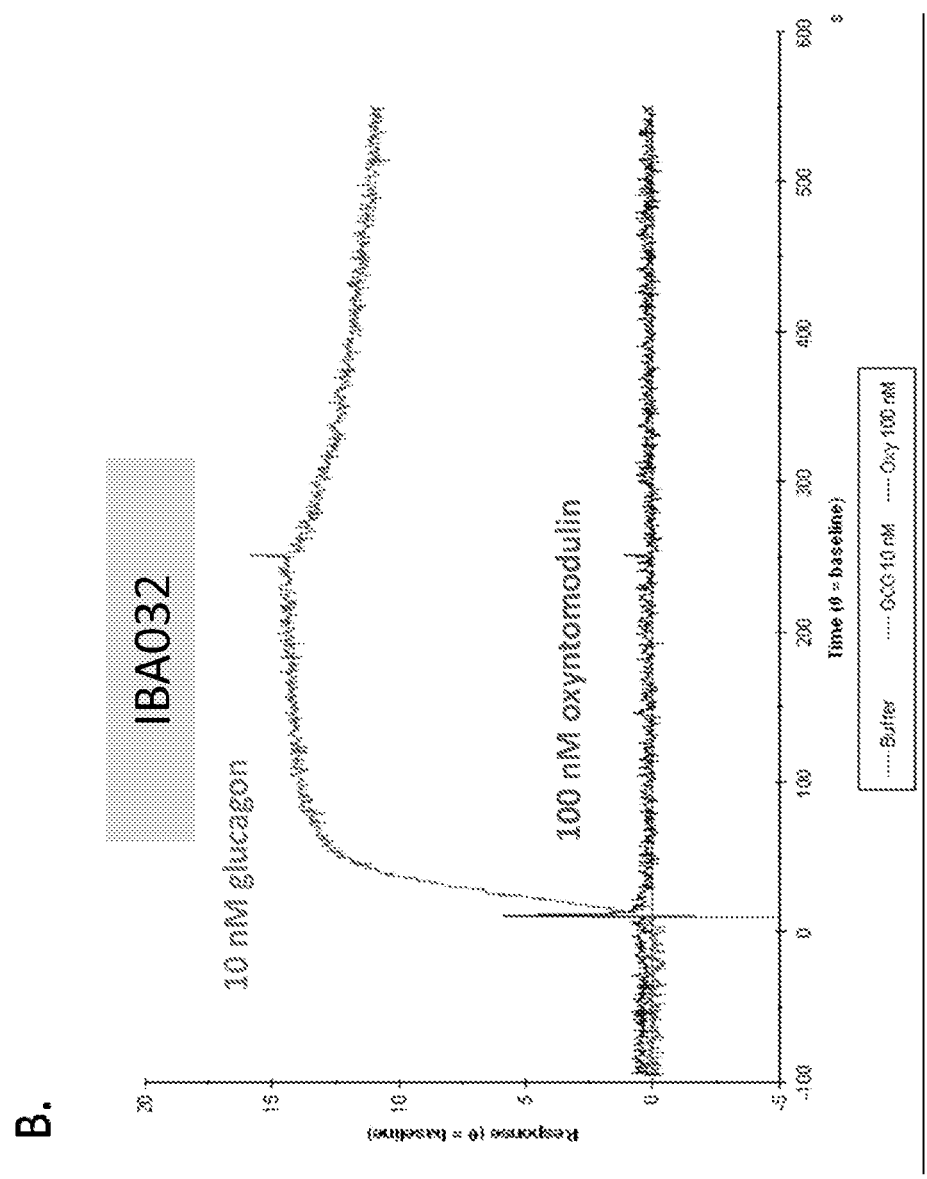
FIG. 1B: Glucagon antibody specificity. (B) Detection/Conjugate antibody IBA032 Biacore analysis. Binding with 10 nM glucagon (labeled as "GCG 10 nM"), 100 nM oxyntomodulin (labeled as "Oxy 100 nM"), and buffer-only negative control (labeled as "buffer") are shown. The detection antibody IBA032 demonstrates no cross-reactivity with oxyntomodulin, and is therefore specific for the C-terminus of glucagon (FIG. 1-B), while at the same time demonstrating a large increase in binding affinity.

As used herein, glucagon refers to glucagon 1-29 of any mammalian species, unless otherwise indicated. The sequence of glucagon is depicted as: HSQGTFTSDYSKY-LDSRRAQDFVQWLMNT, and is also referred to herein as SEQ ID NO: 29.

A full-length antibody is an immunoglobulin molecule comprising two heavy (H) chains and two light (L) chains interconnected by disulfide bonds. The amino terminal portion of each chain includes a variable region of about 100-110 amino acids primarily responsible for antigen recognition via the complementarity determining regions (CDRs) contained therein. The carboxy-terminal portion of each chain defines a constant region primarily responsible for effector function. Light chains are classified as kappa or lambda, which are each characterized by a particular constant region as known in the art. Heavy chains are classified as gamma, mu, alpha, delta, or epsilon, and define the isotype of an antibody as IgG, IgM, IgA, IgD, or IgE, respectively. IgG antibodies can be further divided into subclasses, e.g., IgG1, IgG2, IgG3, IgG4. Each heavy chain type is also characterized by a particular constant region with a sequence well known in the art. "Antigen-binding fragment", as used herein, refers to Fab fragments, Fab' fragments, F(ab')$_2$ fragments, and single chain Fv fragments that bind to glucagon. The term "bind (or 'binds') to glucagon", as used herein, refers to interaction with an epitope of glucagon (SEQ ID NO: 29). The term "epitope" as used herein refers to discrete, three-dimensional sites on an antigen that are recognized by the antibodies or antigen-binding fragments of the present invention.

The CDRs are interspersed with regions that are more conserved, termed framework regions ("FR"). Each light chain variable region (LCVR) and heavy chain variable region (HCVR) is composed of 3 CDRs and 4 FRs, arranged from amino-terminus to carboxy-terminus in the following order: FR1, CDR1, FR2, CDR2, FR3, CDR3, FR4. The 3 CDRs of the light chain are referred to as "LCDR1, LCDR2, and LCDR3" and the 3 CDRs of the heavy chain are referred to as "HCDR1, HCDR2, and HCDR3." The CDRs contain most of the residues which form specific interactions with the antigen. The numbering and positioning of CDR amino acid residues within the LCVR and HCVR regions of the antibodies or antigen-binding fragments of the present invention is determined in accordance with the well-known Kabat numbering convention, or in accordance with Kabat plus Chothia.

As used herein, the term "antibody" refers to a monoclonal antibody unless otherwise indicated. The term "monoclonal antibody", its abbreviation "mAb", and grammatical forms thereof are intended to refer to an antibody that is derived from a single copy or clone including, for example, any eukaryotic, prokaryotic, or phage clone, and not the method by which it is produced. Monoclonal antibodies of the present invention preferably exist in a homogeneous or substantially homogeneous population. Complete mAbs contain two heavy chains and two light chains. "Antigen-binding fragments" of such monoclonal antibodies include, for example, Fab fragments, Fab' fragments, F(ab')$_2$ fragments, single chain Fv fragments, and single domain variable fragments. Monoclonal antibodies and antigen-binding fragments thereof of the present invention can be produced, for example, by recombinant technologies, phage display technologies, synthetic technologies, e.g., CDR-grafting, or combinations of such technologies, or other technologies known in the art. It is understood that regardless of whether antigen-binding fragments are specified, the terms "antibody" and "monoclonal antibody" as used herein includes such fragments, as well as single chain forms, unless indicated otherwise.

Another aspect of the present invention pertains to isolated nucleic acid molecules encoding any of the aforementioned anti-glucagon antibodies, expression vectors comprising the nucleic acid molecules, and host cells comprising the nucleic acid molecules. Additionally, the present invention provides expression vectors containing the polynucleotide sequences previously described operably linked to a control sequence such as an expression sequence, a promoter and/or an enhancer sequence. A variety of expression vectors for the efficient synthesis of antibody polypeptide in pro-karyotic systems, such as bacteria and eukaryotic systems, including but not limited to, yeast and mammalian cell culture systems have been developed. The vectors of the present invention can comprise segments of chromosomal, non-chromosomal and synthetic DNA sequences.

Methods for producing and purifying antibodies and antigen-binding fragments are well known in the art and can be found, for example, in Harlow and Lane (1988) *Antibodies, A Laboratory Manual*, Cold Spring Harbor Laboratory Press, Cold Spring Harbor, New York, chapters 5-8 and 15, ISBN 0-87969-314-2. Antigen-binding fragments can also be prepared by conventional methods. Human framework germline sequences can be obtained from ImMunoGeneTics (IMGT) via their website http://imgt.cines.fr, or from *The Immunoglobulin Facts Book* by Marie-Paule Lefranc and Gerard Lefranc, Academic Press, 2001, ISBN 012441351. The present invention also provides recombinant host cells containing the recombinant vectors previously described. Cell lines of particular preference are selected based on high levels of expression, constitutive expression of protein of interest and minimal contamination from host proteins. Mammalian cell lines available as hosts for expression are well known in the art and include many immortalized cell lines, such as but not limited to, COS-7 cells, Chinese Hamster Ovary (CHO) cells, Baby Hamster Kidney (BHK) cells and many others including cell lines of lymphoid origin such as lymphoma, myeloma, or hybridoma cells. Preferred host cells for transformation of vectors and expression of the antibodies of the present invention are mammalian cells, e.g., NS0 cells (non-secreting (0) mouse myeloma cells), Human embryonic kidney (HEK) 293, SP20 and Chinese hamster ovary (CHO) cells and other cell lines of lymphoid origin such as lymphoma, myeloma, or hybridoma cells. Antibodies of the present invention can be expressed in cell lines other than in hybridomas. Other eukaryotic hosts, such as yeasts, can be alternatively used. The antibodies and more specifically the antigen binding fragments thereof can also be produced from prokaryotic cells such as *Eschericia coli*. Nucleic acids, which comprise a sequence encoding an antibody according to the present invention, can be used for transformation of a suitable mammalian host cell. For example, cDNA sequences encoding a heavy chain (for example, the amino acid sequence given by SEQ ID NO: 27) and a light chain (for example, the amino acid sequence given by SEQ ID NO: 25) may be cloned and engineered into a suitable transient transfection expression vector. The engineered immunoglobulin expression vector may then be transfected into HEK293 cells. Transfectants may be verified for expression of an antibody specifically binding to glucagon.

The present invention further provides methods of purifying any of the aforementioned anti-glucagon antibodies. The engineered antibodies or antigen binding fragments of the present invention may be prepared and purified using known methods. An "isolated" antibody in reference to an anti-glucagon antibody is one that has been identified and separated and/or recovered from a component of its natural environment. Contaminant components of its natural environment are materials that would interfere with diagnostic uses for the antibody, and may include enzymes, hormones, and other proteinaceous or nonproteinaceous solutes. In preferred embodiments, an antibody of the present invention will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. The term "isolated" in reference to an anti-glucagon antibody of the present invention may include the antibody in situ within recombinant cells since at least one component of the antibody's natural environment will not be present. The anti-glucagon antibodies of the present invention may be isolated or purified by any method known in the art, including precipitation by ammonium sulfate or sodium sulfate followed by dialysis against saline, ion exchange chromatography, affinity or immuno-affinity chromatography including, but not limited to Protein-A and/or Protein-G affinity chromatography, as well as gel filtration or zone electrophoresis.

The anti-glucagon antibodies disclosed herein are useful for diagnostic, prognostic, and/or patient monitoring procedures, by detecting the level of glucagon present in or on cells, tissues, or organs, whether in vivo and/or in various forms of ex vivo preparations, and in bodily fluids. The term "bodily fluid" refers to any fluid or fluid-like material derived from the body of a normal or diseased subject, such as blood, serum, plasma, lymph, bone marrow, urine, saliva, tears, cerebrospinal fluid, milk, amniotic fluid, bile, urine, bronchial fluid, ascites fluid, pus, and any other biological fluid product. Also included within the meaning of fluid-like materials are organ or tissue extracts, and culture media in which cells or tissue preparation from a subject have been incubated. An anti-glucagon monoclonal antibody described herein can be conjugated to an enzyme and used in an enzyme-linked immunosorbent assay (ELISA). Such assays are described in detail in, for example, Butler (1994) "ELISA" (Chapter 29), In: van Oss, C. J. et al., eds., *Immunochemistry*, Marcel Dekker, Inc., New York, pp. 759-803. The present anti-glucagon antibodies can also be used in radioimmunoassay and fluorescence-activated cell sorting (FACS) analysis of glucagon expression.

The phrase "specifically binds" as used herein in reference to the affinity of a anti-glucagon antibody for glucagon is intended to mean, unless indicated otherwise, a $K_D$ of preferably less than about $1\times10^{-10}$ M, more preferably between about $1\times10^{-10}$ M and about $1\times10^{-11}$ M, even more preferably, between about $1\times10^{-10}$ M and about $1\times10^{-13}$ M, even more preferably, between about $1\times10^{-11}$ M and about $1\times10^{-13}$ M, as determined by common methods known in the art, including by use of a SPR biosensor essentially as described herein.

As used herein, the term "contacting" refers to the exposing an antibody, for example an antibody of the invention, to a glucagon antigen, for example an analyte in a sample in which the glucagon level is to be determined, for a time and under conditions that permit said monoclonal antibody, or antigen-binding fragment thereof, to bind to glucagon. Such time and conditions are known to one of skill in the art, and/or can be routinely determined by methods known in the art according to references cited herein.

Sensitivity as used herein refers to the lowest level of an analyte (in this case glucagon) that can be measured with acceptable accuracy and precision. Sensitivity is reflected for example by the lower limit of quantitation (LLOQ) which is determined, according to the present invention, by taking a sample of glucagon and diluting it serially until the % CV (coefficient of variation) goes above 20%.

The terms "diabetes" and "diabetic" refer to or describe the physiological conditions in mammals typically characterized by aberrant glucose regulation. Examples include but are not limited to: Type I diabetes, Type II diabetes, hyperglycemia, hyper insulinemia, beta-cell rest, improved beta-cell function by restoring first phase response, prandial hyperglycemia, metabolic syndrome, hypoglycemia, hyper-/hypokalemia, normalizing glucagon levels, obesity as a consequence of diabetes, insulitis, islet transplantation, pediatric diabetes, gestational diabetes, diabetic late complications, micro-/macroalbuminuria, reduced intestinal motility due to glucagon administration, insulin resistance syndromes, syndrome X, glucagonomas, acute pancreatitis, diabetes as a consequence of obesity, diabetic dyslipidemia. Preferably the diabetic condition is type I or type II diabetes. More preferably the diabetic condition is type II diabetes.

Antibody Compositions and Methods

There are well-known methods in the art that a skilled artisan may use to form stable, detectable antigen-antibody complexes (see, e.g., *Antibodies, A Laboratory Manual* by Harlow and Lane (current edition), Cold Spring Harbor Laboratory Press, Cold Spring Harbor, New York, for conditions permitting formation of detectable antigen/antibody complexes).

The anti-glucagon monoclonal antibodies of the present invention or the glucagon/anti-glucagon monoclonal antibody complexes described herein can be detectably labeled using any art-known means (see, e.g., *Antibody Engineering* Volume 2, Kontermann, Roland; Dübel, Stefan (Eds.)). Without limitation, glucagon or a detectably labeled glucagon/anti-glucagon monoclonal antibody complex can be on a cell, or fragment thereof, either in vivo, ex vivo or in vitro. For example, without limitation, such a cell or fragment thereof can be, in situ, isolated from its naturally occurring state, or in a sample, such as, e.g., from a cell pellet, xenograft, tissue, organ, bodily fluid, or any concentrated, purified, enriched form thereof. In any of these methods, the contacting and detecting can each be performed in vitro, or the contacting can be performed in vivo and the detecting can be performed in vitro, or the contacting and the detecting can each be performed in vivo. Labels can be, for example, without limitation, light-emitting or light-absorbing agents, chromophores, chromogens, magnetic or iron particles, dyes, fluorescents, fluorophores, phosphorescents, chemiluminescents, bioluminescents agent, radionuclides, enzymes, positron emission tomographic-imageable agents, magnetic micro-beads, ferrofluid nanoparticles, secondary antibodies, and magnetic resonance-imageable agents.

The term "detectably labeled" means that the anti-glucagon antibody, or antigen-binding fragment thereof of the present invention, or a complex of glucagon/anti-glucagon monoclonal antibody has attached to it, either covalently or non-covalently, a useful detectable label. In direct conjugate-labeled antibody methods, many different useful labels can be employed including, for example, prosthetic group complexes, chromophores, chromogens (color-producing substrates), dyes, fluorescent compounds, fluorogenic compounds, radioactive isotopes, paramagnetic isotopes, and compounds that can be imaged by positron emission tomography (PET) and magnetic resonance imaging (MRI). Useful radiolabels, which are detected simply by gamma counter, scintillation counter, PET scanning, or autoradiography, include $^3$H, $^{124}$I, $^{125}$I, $^{131}$I, $^{35}$S, and $^{14}$C. For in vivo diagnosis, radionuclides can be bound to the mAb or antigen-binding fragments either directly or indirectly using a chelating agent such as DTPA and EDTA. Examples of such radionuclides include $^{99}$Tc, $^{123}$I, $^{125}$I, $^{131}$I, $^{111}$In, $^{97}$Ru, $^{67}$Cu, $^{67}$Ga, $^{68}$Ga, $^{72}$As, $^{89}$Zr, $^{90}$Y and $^{201}$Tl. Other suitable labels are art-known or can be determined by routine experimentation. In indirect methods, a secondary antibody can be conjugated with, for example, an enzyme. Binding of the secondary antibody to the primary antibody, which is bound to the target antigen, can then be detected by reaction with a chromogenic substrate of the enzyme under appropriate conditions to yield a detectable signal.

Colorimetric detection can be used, employing chromogenic compounds that have, or result in, chromophores with high extinction coefficients, and which are therefore easily detectable. When later exposed to its substrate under appropriate reaction conditions, the enzyme will react with the substrate to produce a chemical label that can be detected, for example, by spectrophotometric, fluorometric, or visual means.

Enzymes commonly used for this purpose include horseradish peroxidase, alkaline phosphatase, glucose-6-phosphate dehydrogenase, malate dehydrogenase, staphylococcal nuclease, delta-V-steroid isomerase, yeast alcohol dehydrogenase, α-glycerophosphate dehydrogenase, triose phosphate isomerase, asparaginase, glucose oxidase, β-galactosidase, ribonuclease, urease, catalase, glucoamylase, and acetylcholinesterase. Examples of suitable prosthetic group complexes include, e.g., without limit, streptavidin/biotin and avidin/biotin. Use of chromogens is preferred because assays employing them can be easily performed in clinical diagnostic laboratories and reviewed by a pathologist with equipment commonly available in these laboratories. Commonly used chromogens include diaminobenzidine (DAB); DAB with enhancement; 3-amino-9-ethyl carbazole (AEC); 4-chloro-1-naphthol (4-CN); Hanker-Yates reagent; alpha-naphthol pyronin; 3,3',5,5'-tetramethylbenzidine (TMB); Fast Blue BB; Fast Red TR; new fuchsin; BCIP-NBT; tetrazolium; tetranitoblue tetrazolium (TNBT); and immunogold with silver enhancement.

Useful fluorescent labels include umbelliferone, fluorescein, fluorescein isothiocyanate, dichlorotriazinylamine fluorescein, rhodamine, a dansyl group, phycoerythrin, phycocyanin, allophycocyanin, o-phthaldehyde, fluorescamine, and Cy5 (Haugland ((1996) *Handbook of Fluorescent Probes and Research Chemicals*, Sixth Ed., Molecular Probes, Eugene, Ore.).

The anti-glucagon antibodies, or antigen-binding fragments thereof, or glucagon/anti-glucagon monoclonal antibody complexes of the present invention can also be detectably labeled using fluorescence-emitting metals such as $^{152}Eu^+$, or other members of the lanthanide series, by attaching them using such metal chelating groups as diethylenetriaminepentaacetic acid (DTPA) or ethylenediaminetetraacetic acid (EDTA).

The anti-glucagon antibodies, or antigen-binding fragments thereof, or glucagon/anti-glucagon monoclonal antibody complexes of the present invention can also be detectably labeled by coupling them to a phosphorescent or chemiluminescent compound that can then be detected by the phosphorescence or luminescence that arises during the course of a chemical reaction. Examples of useful chemiluminescent compounds include luminol, isoluminol, theromatic acridinium ester, imidazole, acridinium salt, and oxalate ester. Likewise, a bioluminescent compound such as luciferin, luciferase, or aequorin can be used to label the antibody peptides. The presence of a bioluminescent protein is determined by detecting the presence of luminescence.

The present invention encompasses antibodies recombinantly fused or chemically conjugated (including both covalent and non-covalent conjugations) to a polypeptide (or portion thereof, preferably comprising at least: 10, 20, 30, 40, 50, 60, 70, 80, 90, or 100 contiguous amino acids of the polypeptide) to generate fusion proteins. The fusion does not necessarily need to be direct, but may occur through linker sequences.

A monoclonal antibody, or antigen-binding fragment thereof, of the present invention can also be attached to solid supports, which are particularly useful for immunoassays or purification of a target antigen. Such solid supports include, e.g., without limitation, glass, cellulose, poly-acrylamide, nylon, polystyrene, polyvinyl chloride, or polypropylene.

Antibodies fused or conjugated to a polypeptide may also be used in in vitro immunoassays and in purification methods using known art methods (see e.g., Harbor, et al., supra, and WO 9312 1232; EP 439,095; Naramura et al. (1994) Immunol. Lett. 39:9 1-9; U.S. Pat. No. 5,474,981; Gillies, et al. 1992 PNAS 89:1428-32; Fell, et al. 1991 J. Immunol. 146:2446-52).

The present invention further includes compositions comprising a polypeptide (or fragment thereof) fused or conjugated to an antibody domain other than a variable region. Methods for fusing or conjugating a polypeptide (or fragment thereof) to an antibody or antibody portion are known (see, e.g., U.S. Pat. Nos. 5,336,603; 5,622,929; 5,359,046; 5,349,053; 5,447,851; 5,112,946; EP 307,434; EP 367,166; WO 96/04388; WO9106,570; Ashkenazi, et al. (1991) PNAS 88: 10535-10539; Zheng, et al. (1995) J. Immunol. 154:5590-5600; and Vie, et al. (1992) PNAS 89: 11337-11341).

A polypeptide, polypeptide fragment, may be fused or conjugated to an antibody or antigen-binding fragment thereof described herein to increase the in vivo half-life. Further, a polypeptide, polypeptide fragment, may be fused or conjugated to an antibody or antigen-binding fragment thereof to facilitate purification. In preferred embodiments, the polypeptide is a hexa-histidine peptide, such as the tag provided in a pQE vector (QIAGEN, Inc., Chatsworth, Calif.), among others, many of which are commercially available. Hexa-histidine provides for convenient purification of a protein (Gentz, et al. (1989) PNAS 86:821-824). Other peptide tags useful for purification include, e.g., the "HA" tag, which corresponds to an epitope derived from the influenza hemagglutinin protein (Wilson, et al. (1984) Cell 37:767) and the "flag" tag.

Methods of Using the Antibodies of the Invention

The antibodies of the present invention can be used diagnostically to, for example, monitor the development or progression of diabetes as part of a clinical testing procedure to determine the efficacy of a given treatment regimen using established techniques. The anti-glucagon monoclonal antibodies of the present invention target glucagon regardless of tissue of origin. Because of the relatively greater expression of glucagon on pancreatic alpha cells, it is possible to distinguish alpha cells from pancreatic beta cells or other cells. Also, because of the expression of glucagon by alpha cells, imaging of glucagon may be generally useful for monitoring pancreatic changes in cell-type number and/or distribution. In vivo or in vitro imaging can be used to detect the proliferation, migration, or loss of glucagon expressing or over-expressing cells in a patient. The expression of glucagon can be correlated with disease risk, or disease progression, in pre-diabetic or diabetic patients respectively. Glucagon-targeted imaging could be used to stage the progression of diabetes in pre-diabetic or diabetic patients, or to detect another disease associated with the presence of increased levels of glucagon. An embodiment of the invention provides a method of diagnosing a patient having pre-diabetes for treatment with a glucagon receptor antagonist, or other anti-diabetic agents, comprising: (a) determining the level of glucagon in a bodily fluid by contacting the bodily fluid with an anti-glucagon diagnostic monoclonal antibody, or antigen-binding fragment thereof, that specifically binds to glucagon consisting of the amino acid sequence as in SEQ ID NO: 29, the antibody, or antigen-binding fragment thereof, comprising: light chain complementarity determining regions LCDR1, LCDR2, and LCDR3 comprising the amino acid sequences RSPK-SLVGPMGRTYLY (SEQ ID NO: 15), RRNNLAP (SEQ ID NO: 16), and MQHLEFPLT (SEQ ID NO: 17), respectively, and heavy chain complementarity determining regions HCDR1, HCDR2, and HCDR3 comprising the amino acid sequences GYNFTDYWIH (SEQ ID NO: 18), YFSTHSDYAIINQKFRD (SEQ ID NO: 19), and GGLGLSY (SEQ ID NO: 20), respectively, (b) optionally, removing any non-specifically bound monoclonal antibody or, antigen-binding fragment thereof; and (c) detecting and/or quantifying the amount of monoclonal antibody, or antigen-binding fragment thereof, which is specifically bound to glucagon, wherein the presence of the antibody, or the antigen-binding fragment thereof, specifically bound to glucagon outside the range observed in healthy individuals identifies the diagnosis of pre-diabetes in a patient for selection and treatment with an appropriate glucagon receptor antagonist, or other anti-diabetic agent. Stages of pre-diabetes include, for example impaired fasting glycemia, and impaired glucose tolerance. Impaired fasting glycemia, or impaired fasting glucose (IFG), refers to a condition in which the fasting blood glucose is elevated above what is considered normal levels, but is not high enough to be classified as diabetes mellitus. IFG is considered a pre-diabetic state, associated with insulin resistance and increased risk of cardiovascular pathology, although of lesser risk than impaired glucose tolerance (IGT). Impaired glucose tolerance is a pre-diabetic state of dysglycemia that is associated with insulin resistance, and increased risk of cardiovascular pathology. IGT may precede type 2 diabetes mellitus by many years. Other anti-diabetic agents are known in the art, and include for example, insulins, metformin, a sulfonylurea such as glimepiride, or a DPPIV inhibitor such as sitagliptin.

Glucagon and insulin levels were, for example, used during the development of Sitagliptin. Further, glucagon as a biomarker may also be useful in the diagnosis and/or efficacious treatment of neuro-endocrine tumors (NET) of the pancreas, as well as diagnosis of malignancy in the pancreas (Kolb, A., et al, Glucagon/insulin ratio as a potential biomarker for pancreatic cancer in patients with new-onset diabetes mellitus. Cancer Biol Ther. 2009 August; 8(16):1527-33).

Generally, the amount of labeled antibody needed for detectability in in vivo diagnostic use will vary depending on the patient's age, condition, sex, extent of disease, contraindications, if any, and other variables, and can be readily adjusted by the attending physician or diagnostician. A preferred diagnostic method is radioimmuno-scintigraphic analysis, which is preferably performed in a manner that results in serial total body gamma camera images, and allows determination of regional activity by quantitative "region-of-interest" (ROI) analysis.

For in vivo applications, the detectably-labeled, anti-glucagon antibodies, or antigen-binding fragments thereof, of the present invention can be formulated in convenient forms for administration. For diagnosis, the detectably labeled anti-glucagon antibodies, or antigen-binding fragments thereof, of the present invention can be administered systemically, e.g., parenterally, by injection or infusion. Such injection or infusion can be by any known route, preferably intravenous injection or infusion, subcutaneous injection, intramuscular, intracranial, or intrathecal injection or infusion, or intraperitoneal administration. Injectables can be prepared in conventional forms, either as solutions or suspensions, or as solid forms. Such compositions can be prepared by methods well known in the art. See, e.g., *Remington: The Science and Practice of Pharmacy*, 19$^{th}$ ed. (1995), A. Gennaro et al., Mack Publishing Co., and comprise anti-glucagon antibodies disclosed herein, and a pharmaceutically or diagnostically acceptable carrier, diluent, or excipient. Dosage can vary from 0.01 mg/kg to 100 mg/kg body weight. Further guidance regarding appropriate doses for diagnostic imaging can be found in Smith et al. (1977) *Antibodies in Human Diagnosis and Therapy*, Haber et al., eds., Raven Press, New York, pages 365-389. For in vivo glucagon detection purposes, the term "effective amount" of the present anti-glucagon monoclonal antibody, or antigen-binding fragment thereof, refers to the amount of antibody which, upon single or multiple dose administration to a patient, provides the ability to detect glucagon in vivo.

Use of the Antibodies of the Invention in Immunoassays:

A particular protein such as glucagon can be measured by a variety of immunoassay methods including, e.g., without limitation, competitive and noncompetitive assay systems using techniques such as, e.g., without limitation, Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein A immunoassays. For a review of immunological and immunoassay procedures in general, see for example Stites and Terr (eds.) (1991) *Basic and Clinical Immunology* (7th ed.). Moreover, the immunoassays of the present invention can be performed in many configurations as is known in the art (See for example Maggio (ed.) (1980) *Enzyme Immunoassay* CRC Press, Boca Raton, Fla.; Gosling J P 2000 *Immunoassays: A Practical Approach* (Practical Approach Series) Oxford Univ Press; Diamandis & Christopoulus, 1996 *Immunoassay* Academic Press, San Diego, Calif.).

Immunoassays for quantitation can be performed by a variety of art-known methods. In brief, immunoassays to measure glucagon can be either competitive or noncompetitive binding assays. In competitive binding assays, the sample to be analyzed competes with a labeled analyte for specific binding sites on a capture agent bound to a solid surface. Preferably, the capture agent is an antibody of the present invention, such as IBA032, specifically reactive with the glucagon as described herein. The concentration of labeled analyte bound to the capture agent is inversely proportional to the amount of free analyte present in the sample.

In a competitive binding immunoassay, the target protein present in the sample (i.e., glucagon) competes with labeled glucagon for binding to an antibody, or antigen-binding fragment thereof, of the present invention such as IBA0032. The antibody, or antigen-binding fragment thereof, of the present invention such as IBA032 may be bound to a solid surface to effect separation of bound-labeled protein from the unbound-labeled protein. Alternately, the competitive binding assay may be conducted in liquid phase and a variety of techniques known in the art may be used to separate the bound-labeled protein from the unbound-labeled protein. Following separation, the amount of bound labeled protein is determined. The amount of protein present in the sample is inversely proportional to the amount of labeled protein binding.

Alternatively, a homogeneous immunoassay may be performed in which a separation step is not needed. In these immunoassays, the label on the protein is altered by the binding of the protein to its specific binding composition. This alteration in the labeled protein results in a decrease or increase in the signal emitted by label such that measurement of the label at the end of the immunoassay allows for detection or quantitation of the protein.

Competitive assays are also particularly useful, where the cells are contacted and incubated with a labeled antibody having known binding affinity to the protein, such as $^{125}$I-antibody, and a test sample whose binding affinity to the binding composition is being measured. The bound and free-labeled binding compositions are then separated to assess the degree of protein binding. The amount of test compound bound is inversely proportional to the amount of labeled binding partner binding to the known source. Any one of numerous techniques can be used to separate bound from free protein to assess the degree of protein binding. This separation step could typically involve a procedure such as adhesion to filters followed by washing, adhesion to plastic followed by washing, or centrifugation of the cell membranes.

The ability of an antibody of the present invention to immunoprecipitate a particular antigen can be assessed by, e.g., Western blot analysis. One of skill in the art would be knowledgeable as to the parameters are modifiable to increase binding of an antibody to an antigen and to decrease background (e.g., by pre-clearing the cell lysate with sepharose beads). Further discussion of immunoprecipitation protocols can be found in, e.g., Ausubel et al, eds., 1994, Current Protocols in Molecular Biology, Vol. 1, John Wiley & Sons, Inc., New York.

Use of the Antibodies of the Invention in ELISA:

An ELISA assay comprises preparing an antigen, coating the well of a 96 well microtiter-plate with the antigen, adding the antibody of interest conjugated to a detectable label such as an enzymatic substrate (e.g., horseradish peroxidase or alkaline phosphatase) to the well and incubating for a period of time, and detecting the presence of the antigen. In ELISAs, the antibody of interest does not have to be conjugated to a detectable label; instead, a second antibody (which recognizes the antibody of interest) conjugated to a detectable label may be added to the well. Further, instead of coating the well with the antigen, the capture antibody may be coated to the well. In this case, a second antibody, the detection antibody, which is specific for a distinct non-competing epitope of the analyte, and conjugated to a detectable label, may be added following the addition of the antigen of interest to the coated well. An ordinary artisan can determine without undue experimentation what parameters to adjust, e.g., to increase signal as well as what other variations for an ELISA should be used (see, e.g., Ausubel, et al., eds., 1994, Current Protocols in Molecular Biology, Vol. 1, John Wiley & Sons, Inc., New York).

For example, IBA032 is specific for the c-terminus of the glucagon 1-29 molecule, and may be useful as a glucagon detection antibody for measuring total glucagon in human blood, serum, or plasma if used in conjunction with a glucagon capture antibody, such as IBA009, which is specific for the mid region of the glucagon 1-29 peptide, or other glucagon capture antibodies known in the art.

Alternatively, IBA032 is useful as a glucagon capture antibody for measuring total glucagon in human blood if used in conjunction with a second glucagon detection antibody such as anti-glucagon monoclonal antibodies known in the art. Furthermore, IBA009 may be useful as a glucagon detection antibody for measuring glucagon precursor or partially processed precursor peptides in blood, plasma, or serum, if used in conjunction with other anti-glucagon detection antibodies known in the art.

The binding affinity of an antibody to an antigen and the on- and off-rate of an antibody-antigen interaction can be determined for example by using a competitive binding assay. One non-limiting example is a radioimmunoassay comprising incubating labeled antigen (e.g., using $^3$H or $^{125}$I) with an antibody of interest in the presence of increasing amounts of unlabeled antigen, and then detecting the amount of antibody bound to the labeled antigen. The affinity of the antibody of interest for a particular antigen and the binding off-rates can be determined from the data by, e.g., Scatchard plot analysis. Competition with a second antibody can also be determined using, e.g., radioimmunoassays.

Use of the Antibodies of the Invention in Articles of Manufacture and Kits

The present invention also provides articles of manufacture and kits containing compositions useful for diagnosing, detecting, quantifying, and/or imaging soluble glucagon or glucagon-positive cells. The article of manufacture may comprise a container with a written label. The container may hold a composition comprising the anti-glucagon monoclonal antibody of the present invention, or an antigen-binding fragment thereof, which is either detectably labeled, or unlabeled. The label on the container may indicate that the composition is used for prognosing or monitoring diabetes, or for diagnosing or monitoring particular types of cells that express glucagon, or for monitoring a condition for which glucagon levels are prognostic, or for prediction of an effective target for therapy. In another embodiment, the label may indicate that the composition is useful for detecting and/or quantifying glucagon, and can also indicate directions for either in vivo or in vitro use.

The kit of the present invention can also comprise a container comprising a secondary antibody or even a glucagon antigen, preferably the antigen comprises the c-terminus of human glucagon as in SEQ ID NO: 29. The secondary antibody or glucagon antigen can be conjugated with an enzyme or other label. A chromogenic substrate of the enzyme can also be included in the kit. The kit may further include other materials desirable from a commercial and user standpoint, including buffers, diluents, filters, needles, syringes, and package inserts with instructions for use in vivo, in vitro, or both.

The monoclonal antibodies and antigen-binding fragments thereof of the present invention, are useful in diagnostic procedures and can be used to select and stratify, for example, pre-diabetic and/or diabetic patients, and to monitor patient responses to glucagon receptor antagonists or other diabetes therapeutics using blood or tissue samples collected by routine methods.

The present methods thus offer newly diagnosed diabetes patients a form of risk stratification that uses noninvasive means to assess the probability that a given condition may subsequently progress to diabetes. Such information improves the ability to design appropriate monitoring and therapy protocols on an individual patient basis.

The glucagon antibodies or glucagon/anti-glucagon monoclonal antibody complexes of the present invention and methods disclosed herein can be used in the diagnosis of a variety of mammalian species, and are equally applicable in the practice of human or veterinary medicine. Thus, these antibodies, complexes, and methods may be used with domestic and commercial animals, and most preferably, with humans.

The following examples are offered for illustrative purposes only, and are not intended to limit the scope of the present invention.

EXAMPLE 1

Antibody Expression and Purification

A panel of murine anti-glucagon antibodies is obtained using standard hybridoma technology, and screened to identify a pair of reagents that could be used to develop an ELISA-based assay. Mutations are systematically introduced into individual complementarity determining regions (CDRs) of each antibody and the resulting libraries are subjected to multiple rounds of selection with decreasing concentrations of antigen and/or increasing periods of dissociation to isolate clones with improved affinities. The sequences of individual variants are determined and used to construct a combinatorial library which is subjected to further rounds of selection with increased stringency to identify additive or synergistic mutational pairings between the individual CDR regions. Individual combinatorial clones are sequenced and binding characteristics are determined.

Engineered and/or optimized anti-glucagon antibodies referred to herein as IBA009 and IBA032 are obtained, having the amino acid sequences of the variable regions of the heavy chain and light chain, and the complete heavy chain and light chain amino acid sequences, and the nucleotide sequences encoding the same, as listed below in the section entitled "Amino Acid and Nucleotide Sequences". The sequence ID's corresponding to these fragments are shown below in Table 1, as well as the light chain and heavy chain CDR amino acid sequences.

Table 1A-1D.

A. CDR Amino Acid Sequences of Antibody IBA009

| CDRs | Amino Acid Sequences |
| --- | --- |
| IBA009 LCDR 1 | KASENAGTYVA (SEQ ID NO: 1) |
| IBA009 LCDR 2 | NGSHRYD (SEQ ID NO: 2) |
| IBA009 LCDR 3 | GQSYSYPWT (SEQ ID NO: 3) |
| IBA009 HCDR 1 | GYNFNDYWLN (SEQ ID NO: 4) |
| IBA009 HCDR 2 | NAYPGWGIINYNEKFKS (SEQ ID NO: 5) |
| IBA009 HCDR 3 | DYDNAY (SEQ ID NO: 6) |

B. CDR Amino Acid Sequences of Antibody IBA032

| CDRs | Amino Acid Sequences |
| --- | --- |
| IBA032 LCDR 1 | RSPKSLVGPMGRTYLY (SEQ ID NO: 15) |
| IBA032 LCDR 2 | RRNNLAP (SEQ ID NO: 16) |
| IBA032 LCDR 3 | MQHLEFPLT (SEQ ID NO: 17) |
| IBA032 HCDR 1 | GYNFTDYWIH (SEQ ID NO: 18) |
| IBA032 HCDR 2 | YFSTHSDYAIINQKFRD (SEQ ID NO: 19) |
| IBA032 HCDR 3 | GGLGLSY (SEQ ID NO: 20) |

C. IBA009 and IBA032 Amino Acid Sequences

| mAb Fragment | Amino Acid Sequences |
| --- | --- |
| IBA009 LCVR | SEQ ID NO: 7 |
| IBA009 HCVR | SEQ ID NO: 9 |
| IBA009 LC | SEQ ID NO: 11 |
| IBA009 HC | SEQ ID NO: 13 |
| IBA032 LCVR | SEQ ID NO: 21 |
| IBA032 HCVR | SEQ ID NO: 23 |
| IBA032 LC | SEQ ID NO: 25 |
| IBA032 HC | SEQ ID NO: 27 |

D. cDNA sequences encoding IBA009 and IBA032 amino acid sequences:

| mAb Fragment | cDNA sequence encoding the named fragment |
| --- | --- |
| IBA009 LCVR | SEQ ID NO: 8 |
| IBA009 HCVR | SEQ ID NO: 10 |
| IBA009 LC | SEQ ID NO: 12 |
| IBA009 HC | SEQ ID NO: 14 |
| IBA032 LCVR | SEQ ID NO: 22 |
| IBA032 HCVR | SEQ ID NO: 24 |
| IBA032 LC | SEQ ID NO: 26 |
| IBA032 HC | SEQ ID NO: 28 |

The anti-glucagon antibodies of the present invention, or antigen binding fragments thereof, including but not limited to IBA009 (SEQ ID NO: 12 and SEQ ID NO: 14), and IBA032 (SEQ ID NO: 26 and SEQ ID NO: 28), may be transiently expressed, using vectors known in the art to be suitable for expression in HEK293 EBNA cells (Edge BioSystems, #90500130), following standard transfection procedures. Briefly, a recombinant vector or vectors comprising SEQ ID NO: 12 and SEQ ID NO: 14, or SEQ ID NO: 26 and SEQ ID NO: 28, may be constructed and used to transiently transfect HEK293 EBNA cells. Transfected cells are cultured in standard serum-free medium containing geneticin (G418) and tobramycin for 48 to 120 hours at 37° C. after transfection. The anti-glucagon antibody may be purified on a 60 ml rProtein A Sepharose column (Amersham Biosciences; #17-1279-04) by following the manufacturer's instructions, and further concentrated and purified by size exclusion chromatography (XK50/60 Superdex200, Pharmacia) with phosphate buffered saline (PBS), pH 7.4, as the mobile phase. Next, the antibody preparation may be filtered using a Millev-GV, PVDF membrane, 0.22 µm, 33 mm, (Millipore; #SLGV033RS) and stored at 4 to 8° C. or frozen at −20 to −80° C.

EXAMPLE 2

Binding Kinetics and Affinity of Antibodies IBA009 and IBA032

The binding kinetics of anti-glucagon monoclonal antibodies of the present invention to glucagon may be determined by use of a surface plasmon resonance biosensor such as a BIAcore® 2000, BIAcore® 3000, or a BIAcore® T100 (GE Health Care, Piscataway, N.J.) according to methods known in the art. Except as noted, all reagents and materials may be purchased from Biacore®, and measurements may be performed at 25° C.

Briefly described, the anti-glucagon monoclonal antibody IBA009 or IBA032, may be dissolved in HBS-EP buffer (150 mM sodium chloride, 3 mM EDTA, 0.005% (w/v) surfactant P-20, and 10 mM N-2-hydroxyethylpiperazine-N'-2-ethanesulfonic acid (HEPES) at pH 7.4; #BR-1001-88). Goat anti-mouse Fc antibody is immobilized on flow cells 1 to 4 of a CM5 sensor chip at a level of 4000 response units (RUs) using amine coupling chemistry to capture anti-glucagon antibodies.

Binding may be evaluated using multiple analytical cycles. Each cycle is performed at a flow rate of 50 µl/minute, and may consist of the following steps: injection of about 10 µl of the anti-glucagon monoclonal antibody IBA009 or IBA032 at 10 µg/ml aiming at a capture of 40-100 RUs, injection of 250 µl of glucagon (1-29) (Anaspec 22456)—(starting at 100 nM and using two-fold serial dilutions for each cycle) followed by 20 minutes for dissociation, and regeneration using about 30 µl of 10 mM glycine hydrochloride, pH 1.5. Association and dissociation rates for each cycle may be evaluated using a "1:1 (Langmuir) binding" model in the BIAevaluation software 4.1.

The anti-glucagon monoclonal antibodies IBA009 and IBA032 may be tested for binding kinetics to glucagon. As shown in Table 2 below, IBA009 and IBA032 bind glucagon with very high binding affinity ($K_D$). Table 2 also displays $k_{on}$ and $k_{off}$ rate data. The antibody IBA009 of Example 1 was determined to have a $K_D$ of $7.3 \times 10^{-13}$ M. The antibody IBA032 of Example 1 was determined to have a $K_D$ of $8.7 \times 10^{-12}$ M. These data indicate that antibodies IBA009 and IBA032 each bind glucagon with high affinity. IBA009 demonstrates an affinity for glucagon about 130 fold stronger than an anti-glucagon antibody known in the art as 2D3-2B11 (commercially available from Sigma-Aldrich, product number WH0002641M1). IBA032 demonstrates an affinity for glucagon about 800 fold stronger than an anti-glucagon antibody known in the art as K79bB10 (commercially available from Sigma-Aldrich, product number G2654).

TABLE 2

Binding Kinetics and Affinity of Antibodies IBA009 and IBA032

| Antibody | $k_{on}$ (1/Ms) | $k_{off}$ (1/s) | $K_D$ (M)[a] |
|---|---|---|---|
| IBA009 | $1.5 \times 10^7$ | $1.1 \times 10^{-5}$ | $7.3 \times 10^{-13}$ |
| IBA032 | $2.7 \times 10^7$ | $2.4 \times 10^{-4}$ | $8.7 \times 10^{-12}$ |

[a]Calculated as $K_D = k_{off}/k_{on}$

EXAMPLE 3

Human Glucagon ELISA Using IBA009 and IBA032

The antibodies IBA009 and IBA032 of Example 1 are utilized to develop and validate an enzyme-linked immunosorbent assay (ELISA) for glucagon levels in patients. The glucagon sandwich ELISA is performed on MSD Streptavidin 96-well plates that are washed three times with TBST (Tris buffered saline containing 10 mmol/L Tris pH 7.40, 150 mmol/L NaCl with 1 mL Tween 20/L) and blocked with 1% Ovalbumin (Sigma) in TBS for one hour at room temperature. Following washing of the plate, 50 µL of biotin-labeled IBA009 capture antibody (1 µg/mL) is added and allowed to bind to the plate for one hour with gentle shaking. Afterward, the wells are washed three times with TBST, and 100 µL of glucagon standards consisting of varying concentrations of glucagon protein (e.g., SEQ ID NO: 29) in assay buffer consisting of 50 mmol/L HEPES, pH 7.40, 150 mmol/L NaCl, 10 mL/L Triton X-100, 5 mmol/L EDTA, and 5 mmol/L EGTA and 1% ovalbumin, which is supplemented with 100 µg/mL Heterophilic Blocking Reagent (Scantibodies) are added to the wells to generate a calibration curve. Plasma samples are diluted 1:8 in the same assay buffer, added to their respective wells, and incubated for 2.5 hours at room temperature with gentle rocking. Following aspiration, wells are washed 3 times with TBST, and 50 µL of 1 µg/mL ruthenium-labeled conjugate glucagon-specific detection antibody IBA032 are added to the wells, which are incubated for 2.5 hours at room temperature. The plate is again washed three times with TBST, and 150 µl of 2X-MSD Read Buffer T is added to the wells. The plate is then read on an MSD reader which records ruthenium electrochemiluminescence. Concentrations of glucagon in samples are interpolated against a standard curve made up of reference standard glucagon (Eli Lilly and Company) using a 4 PL fit (MSD discovery workbench). MesoScale Discovery software is used for fitting ELISA calibration curves and enterpolation of unknown values (See FIG. 2).

Specificity of the ELISA for other closely related members of the incretin peptide superfamily may be also tested using oxyntomodulin, GIP, GLP-1, GLP-2, secretin and vasoactive intestinal peptide, for example, with each at a concentration of 100 ng/mL. No cross-reactivity is observed with any of these other peptides, indicating that the ELISA of Example 3 possesses specificity for glucagon. The ELISA of the present invention demonstrates excellent recovery, precision, and linearity, and a broad dynamic range of 0.14 pmol/L to 1950 pmol/L. The LLOQ at a CV of 20% is determined to be 0.14 pmol/L. Since samples are diluted 1:8 prior to analysis, this corresponds to a reportable lower limit of 1.12 pmol/L.

Fifty eight healthy single donor plasma samples are analyzed to establish a reference range. The mean glucagon level is determined to be 13.1±0.7 pmol/L with an observed range from 5.3 to 37.4 pmol/L, demonstrating that the ELISA has more than adequate sensitivity to detect glucagon levels in normal individuals.

Measurement of glucagon in plasma from normal healthy subjects following acetone extraction gives a mean value of 12 pmol/L (Von Schenck H, Nilsson O R. Radioimmunoassay of extracted glucagon compared with three non-extraction assays. Clinica Chimica Acta 1981; 109:183-191), which agrees with the values obtained from similar samples measured in the ELISA of Example 3.

The use of high affinity engineered monoclonal antibodies of the present invention in a sandwich ELISA format provides a robust, sensitive, and convenient high throughput method for measuring concentrations of glucagon that is highly sensitive and specific. The ELISA method described herein has several advantages over currently available RIA methods. First, the assay uses two high affinity monoclonal antibodies which bind to glucagon. This allows for sustainable production of the monoclonal antibodies and does not rely upon polyclonal antisera. Avoidance of polyclonal antisera overcomes the problem of limited quantities of a batch of polyclonal sera, and the variable quality of such antisera batch to batch. An ELISA of the present invention comprising IBA032 and IBA009 offers several significant advantages over the currently available radioimmunoassay (RIA) kits from Alpco and Millipore. For instance, plasma glucagon levels as measured by RIA have been shown to vary depending on the particular antisera used. RIA methods in the art utilizing C-terminal-directed polyclonal antisera have especially short dynamic ranges (approx 5 pmol/L to 150 pmol/L), most likely due to the conserved nature of the glucagon peptide and thus poor immunogenicity. In contrast, with the sandwich ELISA of Example 3, utilization of high affinity optimized monoclonal antibodies and the Mesoscale Discovery (MSD) electrochemiluminescent (ECL) format provides an assay with extended range and superior sensitivity. Further, in contrast to RIA's that must be run in glass tubes, the 96-well plate-based assay format of Example 3 makes it possible to have greater throughput and better automation. In addition, the sandwich ELISA of Example 3 further avoids the costs associated with radioactive waste, the short expiration time of the labeled tracer, and the lot to lot variation of tracer that must be manufactured every one to two months.

Another advantage of the present monoclonal antibodies is the c-terminal specificity of antibody IBA032, which results in a lack of binding of this antibody to oxyntomodulin. Oxyntomodulin is a peptide that contains the glucagon 1-29 sequence, plus an 8 amino acid carboxyterminal extension, and can create a source of false positive signal in other glucagon assays known in the art which lack this c-terminal specificity.

The assay demonstrates increased sensitivity, being approximately 10× more sensitive than methods known in the art. Further, the ELISA requires less sample volume, approximately 10× less, and requires less time to complete the assay, approximately 6 hrs as compared to 3 days for an RIA. In addition, the ELISA of the present invention demonstrates robust dynamic range, avoiding the problem experienced when sample levels exceed the quantitation range on the high end of the RIA method of the art, and thus require an additional freeze-thaw and rerunning at a higher dilution which often leads to inconsistent results.

Figure 2:
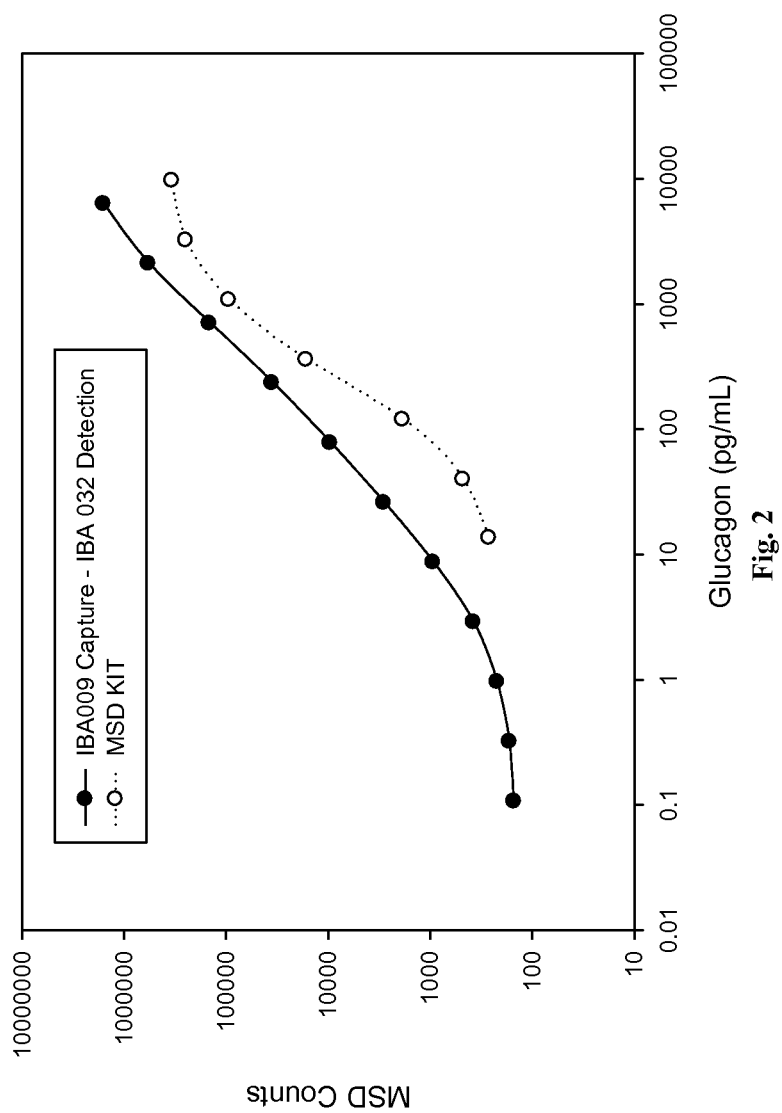
FIG. 2: Development of the glucagon sandwich ELISA method.
Figure 3:
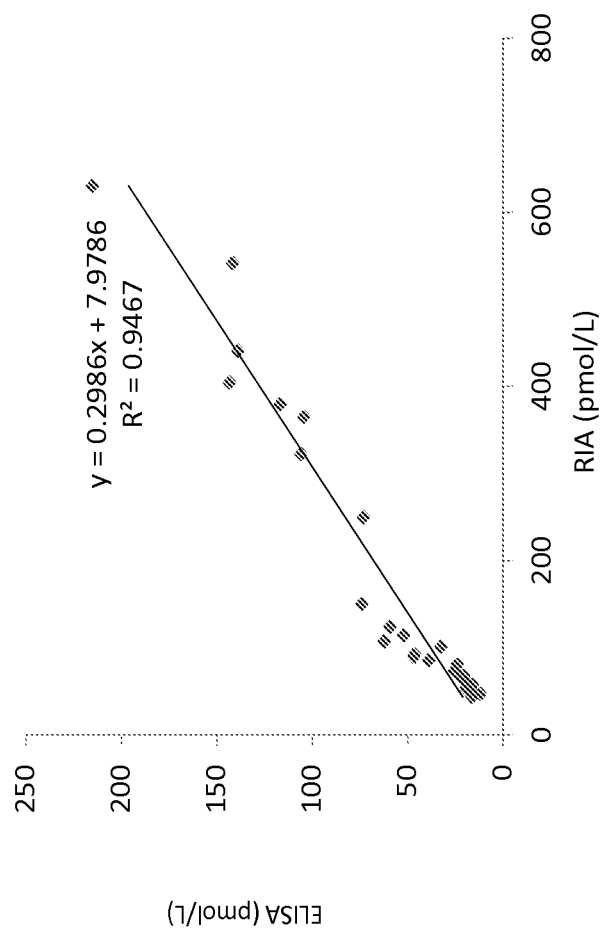
FIG. 3: Correlation of glucagon concentrations.

The ELISA of the present invention likewise demonstrates advantages over the commercially available kit from Meso Scale Discovery (MSD), due to increased sensitivity and dynamic range as shown in FIG. 2. The ELISA of the present invention demonstrates surprisingly improved sensitivity and is capable of detecting baseline glucagon in plasma and/or serum samples at levels below those reported to be testable with the existing MSD glucagon assay kit. Further, the ELISA of the present invention can detect relatively small changes in glucagon levels over a remarkably wide range (over 4 logs) of glucagon concentrations. The ELISA of the present invention exhibits sensitivity such that the typical dilution is a 1:8, and the resulting 12.5% serum or plasma matrix and 87.5% buffer concentrations minimize confounding cross-reactivity also known as "matrix interference".

Amino Acid and Nucleotide Sequences

<SEQ ID NO: 1; PRT1; Artificial> [IBA009 LCDR1]
KASENAGTYVA

<SEQ ID NO: 2; PRT1; Artificial> [IBA009 LCDR2]
NGSHRYD

<SEQ ID NO: 3; PRT1; Artificial> [IBA009 LCDR3]
GQSYSYPWT

<SEQ ID NO: 4; PRT1; Artificial> [IBA009 HCDR1]
GYNFNDYWLN

<SEQ ID NO: 5; PRT1; Artificial> [IBA009 HCDR2]
NAYPGWGIINYNEKFKS

<SEQ ID NO: 6; PRT1; Artificial> [IBA009 HCDR3]
DYDNAY

<SEQ ID NO: 7; PRT1; Artificial> [IBA009 LCVR]
NIVMTQSPKSMSMSVGERVTLTCKASENAGTYVAWYQQKPEQSPKLLIY
NGSHRYDGVPDRFTGSGSATDFTLTISSVQAEDLADYYCGQSYSYPWTF
GGGTKLEMKR <SEQ ID NO: 8; DNA; Artificial> [IBA009 LCVR]
AACATTGTGATGACCCAGAGCCCGAAAAGCATGAGCATGAGCGTGGGCG
AACGTGTGACCCTGACCTGCAAAGCGAGCGAGAACGCTGGCACCTATGT
TGCGTGGTATCAGCAGAAACCGGAACAGTCTCCGAAACTGCTGATCTAT
AATGGGAGCCACCGGTATGACGGCGTGCCGGATCGTTTTACCGGCAGCG
GCAGCGCGACCGATTTCACCCTGACCATTAGCAGCGTGCAGGCGGAAGA
TCTGGCGGATTATTACTGCGGCCAGAGCTATAGCTATCCGTGGACCTTT
GGCGGTGGGACCAAGCTGGAAATGAAACGG <SEQ ID NO: 9; PRT1; Artificial> [IBA009 HCVR]
QVQLLQPGAELVKPGASVKLSCKASGYNFNDYWLNWVKQRPGQGLEWIG
NAYPGWGIINYNEKFKSKVTLTVDTSSSTVYMQLSSLTSDDSAVYYCAR
DYDNAYWGQGTTVTVSS <SEQ ID NO: 10; DNA; Artificial> [IBA009 HCVR]
CAGGTGCAGCTGCTGCAGCCGGGTGCCGAACTGGTTAAACCGGGTGCCA
GCGTGAAACTGAGCTGCAAAGCGAGCGGCTATAACTTCAACGACTATTG
GCTTAACTGGGTGAAACAGCGTCCGGGCCAGGGCCTGGAATGGATTGGC
AATGCCTATCCGGGCTGGGGCATCATTAACTATAACGAAAAATTCAAA
GCAAAGTGACCCTGACCGTGGATACCAGCAGCAGCACCGTGTATATGCA
GCTGTCTAGCCTGACCAGCGATGATAGCGCGGTGTATTATTGCGCGCGT
GATTATGATAACGCGTATTGGGGTCAGGGCACCACGGTCACCGTCTCCT
CA <SEQ ID NO: 11; PRT1; Artificial> [IBA009 LC]
NIVMTQSPKSMSMSVGERVTLTCKASENAGTYVAWYQQKPEQSPKLLIY
NGSHRYDGVPDRFTGSGSATDFTLTISSVQAEDLADYYCGQSYSYPWTF
GGGTKLEMKRADAAPTVSIFPPSSEQLTSGGASVVCFLNNFYPKDINVK
WKIDGSERQNGVLNSWTDQDSKDSTYSMSSTLTLTKDEYERHNSYTCEA
THKTSTSPIVKSFNRNEC <SEQ ID NO: 12; DNA; Artificial> [IBA0091 LC]
AACATTGTGATGACCCAGAGCCCGAAAAGCATGAGCATGAGCGTGGGCG
AACGTGTGACCCTGACCTGCAAAGCGAGCGAGAACGCTGGCACCTATGT
TGCGTGGTATCAGCAGAAACCGGAACAGTCTCCGAAACTGCTGATCTAT
AATGGGAGCCACCGGTATGACGGCGTGCCGGATCGTTTTACCGGCAGCG
GCAGCGCGACCGATTTCACCCTGACCATTAGCAGCGTGCAGGCGGAAGA
TCTGGCGGATTATTACTGCGGCCAGAGCTATAGCTATCCGTGGACCTTT
GGCGGTGGGACCAAGCTGGAAATGAAACGGGCTGATGCGGCGCCAACTG
TATCCATCTTCCCACCATCCAGTGAGCAGTTAACATCTGGAGGTGCCTC
AGTCGTGTGCTTCTTGAACAACTTCTACCCCAAAGACATCAATGTCAAG
TGGAAGATTGATGGCAGTGAACGACAAAATGGCGTCCTGAACAGTTGGA
CTGATCAGGACAGCAAAGACAGCACCTACAGCATGAGCAGCACCCTCAC
GTTGACCAAGGACGAGTATGAACGACATAACAGCTATACCTGTGAGGCC
ACTCACAAGACATCAACTTCACCCATTGTCAAGAGCTTCAACAGGAATG
AGTGT <SEQ ID NO: 13; PRT1; Artificial> [IBA009 HC]
QVQLLQPGAELVKPGASVKLSCKASGYNFNDYWLNWVKQRPGQGLEWIG
NAYPGWGIINYNEKFKSKVTLTVDTSSSTVYMQLSSLTSDDSAVYYCAR
DYDNAYWGQGTTVTVSSAKTTPPSVYPLAPGSAAQINSMVTLGCLVKGY
FPEPVTVTWNSGSLSSGVHTFPAVLQSDLYTLSSSVTVPSSTWPSETVT
CNVAHPASSTKVDKKIVPRDCGCKPCICTVPEVSSVFIFPPKPKDVLTI
TLTPKVTCVVVDISKDDPEVQFSWFVDDVEVHTAQTQPREEQFNSTFRS
VSELPIMHQDWLNGKEFKCRVNSAAFPAPIEKTISKTKGRPKAPQVYTI
PPPKEQMAKDKVSLTCMITDFFPEDITVEWQWNGQPAENYKNTQPIMDT
DGSYFVYSKLNVQKSNWEAGNTFTCSVLHEGLHNHHTEKSLSHSPGK

Amino Acid and Nucleotide Sequences

<SEQ ID NO: 14; DNA; Artificial> [IBA009 HC]
CAGGTGCAGCTGCTGCAGCCGGGTGCCGAACTGGTTAAACCGGGTGCCA
GCGTGAAACTGAGCTGCAAAGCGAGCGGCTATAACTTCAACGACTATTG
GCTTAACTGGGTGAAACAGCGTCCGGGCCAGGGCCTGGAATGGATTGGC
AATGCCTATCCGGGCTGGGGCATCATTAACTATAACGAAAAATTCAAAA
GCAAAGTGACCCTGACCGTGGATACCAGCAGCAGCACCGTGTATATGCA
GCTGTCTAGCCTGACCAGCGATGATAGCGCGGTGTATTATTGCGCGCGT
GATTATGATAACGCGTATTGGGGTCAGGGCACCACGGTCACCGTCTCCT
CAGCCAAAACGACACCCCCATCTGTCTATCCGCTAGCCCCTGGATCTGC
CGCCCAGACCAACAGCATGGTGACCCTGGGCTGTCTGGTGAAGGGCTAC
TTCCCTGAGCCTGTGACAGTGACCTGGAACAGCGGCTCTCTGTCTAGCG
GCGTGCACACATTCCCTGCCGTGCTGCAGAGCGACCTGTACACCCTGAG
CAGCAGCGTGACCGTGCCTAGCAGCACATGGCCTAGCGAGACCGTGACA
TGCAACGTGGCCCACCCTGCCTCTTCTACCAAGGTGGACAAGAAGATCG
TGCCCAGAGACTGCGGCTGCAAGCCTTGCATCTGCACCGTGCCTGAGGT
GAGCAGCGTGTTCATCTTCCCACCCAAGCCCAAGGACGTGCTCACCATC
ACCCTCACCCCCAAGGTCACGTGTGTTGTGGTAGACATCAGCAAGGATG
ATCCCGAGGTCCAGTTCAGCTGGTTTGTAGATGATGTGGAGGTGCACAC
AGCTCAGACGCAACCCCGGGAGGAGCAGTTCAACAGCACTTTCCGCTCA
GTCAGTGAACTTCCCATCATGCACCAGGACTGGCTCAATGGCAAGGAGT
TCAAATGCAGGGTCAACAGTGCAGCTTTCCCTGCCCCCATCGAGAAAAC
CATCTCCAAAACCAAAGGCAGACCGAAGGCTCCACAGGTGTACACCATT
CCACCTCCCAAGGAGCAGATGGCCAAGGATAAAGTCAGTCTGACCTGCA
TGATAACAGACTTCTTCCCTGAAGCATTACTGTGGAGTGGCAGTGGAA
TGGGCAGCCAGCGGAGAACTACAAGAACACTCAGCCCATCATGGACACA
GATGGCTCTTACTTCGTCTACAGCAAGCTCAATGTGCAGAAGAGCAACT
GGGAGGCAGGAAATACTTTCACCTGCTCTGTGTTACATGAGGGCCTGCA
CAACCACCATACTGAGAAGAGCCTCTCCCACTCTCCTGGTAAA <SEQ ID NO: 15; PRT1; Artificial> [IBA032 LCDR1]
RSPKSLVGPMGRTYLY <SEQ ID NO: 16; PRT1; Artificial> [IBA032 LCDR2]
RRNNLAP <SEQ ID NO: 17; PRT1; Artificial> [IBA032 LCDR3]
MQHLEFPLT <SEQ ID NO: 18; PRT1; Artificial> [IBA032 HCDR1]
GYNFTDYWIH <SEQ ID NO: 19; PRT1; Artificial> [IBA032 HCDR2]
YFSTHSDYAIINQKFRD <SEQ ID NO: 20; PRT1; Artificial> [IBA032 HCDR3]
GGLGLSY <SEQ ID NO: 21; PRT1; Artificial> [IBA032 LCVR]
DIVMTQAAPSVLVTPGESVSISCRSPKSLVGPMGRTYLYWFLQRPGQSP
QLLIYRRNNLAPGVPDRFSGSGSGTAFTLRISRVEAEDVGIYYCMQHLE
FPLTFGAGTKLEIKR <SEQ ID NO: 22; DNA; Artificial> [IBA032 LCVR]
GATATTGTGATGACCCAGGCAGCGCCGAGCGTTCTGGTTACCCCGGGTG
AAAGCGTGAGCATTAGCTGCCGAAGCCCAAAAAGCCTAGTGGGTCCCAT
GGGAAGGACCTATCTATATTGGTTTCTGCAGCGTCCGGGTCAGAGCCCG
CAGCTGCTGATTTATCGTCGGAACAACCTGGCACCAGGTGTGCCGGATC
GTTTTAGCGGCAGCGGTAGCGGCACCGCGTTTACCCTGCGTATTAGCCG
TGTGGAAGCGGAAGATGTGGGCATTTATTATTGCATGCAGCACCTGGAA
TTCCCGCTGACCTTTGGTGCGGGCACCAAGCTGGAAATCAAACGG <SEQ ID NO: 23; PRT1; Artificial> [IBA032 HCVR]
QVQLQQSGAELVKPGASVKMSCKASGYNFTDYWIHWVKERPGQGLEWIG
YFSTHSDYAIINQKFRDKATLTADKSSRLAYMQLSSLTSEDSAIYYCAR
GGLGLSYWGQGTTVTVSS <SEQ ID NO: 24; DNA; Artificial> [IBA032 HCVR]
CAGGTGCAGCTGCAGCAGAGCGGTGCGGAACTGGTGAAACCGGGTGCGA
GCGTGAAAATGAGCTGCAAAGCGAGCGGCTATAACTTTACAGATTATTG
GATTCACTGGGTGAAAGAACGTCCGGGCCAGGGCCTGGAATGGATTGGC
TATTTTAGTACGCATAGCGATTATGCCATCATTAACCAGAAATTCAGAG
ATAAAGCGACCCTGACCGCGGATAAAAGCAGCCGTCTGGCCTATATGCA
GCTGTCTAGCCTGACCAGCGAAGATAGCGCGATTTATTACTGCGCGCGT
GGCGGCTTAGGCCTGAGCTATTGGGGCCAGGGTACCACGGTCACAGTCT
CCTCA <SEQ ID NO: 25; PRT1; Artificial> [IBA032 LC]
DIVMTQAAPSVLVTPGESVSISCRSPKSLVGPMGRTYLYWFLQRPGQSP
QLLIYRRNNLAPGVPDRFSGSGSGTAFTLRISRVEAEDVGIYYCMQHLE
FPLTFGAGTKLEIKRADAAPTVSIFPPSSEQLTSGGASVVCFLNNFYPK
DINVKWKIDGSERQNGVLNSWTDQDSKDSTYSMSSTLTLTKDEYERHNS
YTCEATHKTSTSPIVKSFNRNEC <SEQ ID NO: 26; DNA; Artificial> [IBA032 LC]
GATATTGTGATGACCCAGGCAGCGCCGAGCGTTCTGGTTACCCCGGGTG
AAAGCGTGAGCATTAGCTGCCGAAGCCCAAAAAGCCTAGTGGGTCCCAT
GGGAAGGACCTATCTATATTGGTTTCTGCAGCGTCCGGGTCAGAGCCCG
CAGCTGCTGATTTATCGTCGGAACAACCTGGCACCAGGTGTGCCGGATC
GTTTTAGCGGCAGCGGTAGCGGCACCGCGTTTACCCTGCGTATTAGCCG
TGTGGAAGCGGAAGATGTGGGCATTTATTATTGCATGCAGCACCTGGAA
TTCCCGCTGACCTTTGGTGCGGGCACCAAGCTGGAAATCAAACGGGCTG
ATGCGGCGCCCACTGTATCCATCTTCCCACCATCCAGTGAGCAGTTAAC
ATCTGGAGGTGCTAGCGTCGTGTGCTTCTTGAACAACTTCTACCCCAAA
GACATCAATGTCAAGTGGAAGATTGATGGCAGTGAACGACAAAATGGCG
TCCTGAACAGTTGGACTGATCAGGACAGCAAAGACAGCACCTACAGCAT
GAGCAGCACCCTCACGTTGACCAAGGACGAGTATGAACGACATAACAGC
TATACCTGTGAGGCCACTCACAAGACATCAACTTCACCCATTGTCAAGA
GCTTCAACAGGAATGAGTGT <SEQ ID NO: 27; PRT1; Artificial> [IBA032 HC]
QVQLQQSGAELVKPGASVKMSCKASGYNFTDYWIHWVKERPGQGLEWIG
YFSTHSDYAIINQKFRDKATLTADKSSRLAYMQLSSLTSEDSAIYYCAR
GGLGLSYWGQGTTVTVSSAKTTPPSVYPLAPGSAAQTNSMVTLGCLVKG
YFPEPVTVTWNSGSLSSGVHTFPAVLQSDLYTLSSSVTVPSSTWPSETV
TCNVAHPASSTKVDKKIVPRDCGCKPCICTVPEVSSVFIFPPKPKDVLT
ITLTPKVTCVVVDISKDDPEVQFSWFVDDVEVHTAQTQPREEQENSTFR
SVSELPIMHQDWLNGKEFKCRVNSAAFPAPIEKTISKTKGRPKAPQVYT
IPPPKEQMAKDKVSLTCMITDFFPEDITVEWQWNGQPAENYKNTQPIMD
TDGSYFVYSKLNVQKSNWEAGNTFTCSVLHEGLHNHHTEKSLSHSPGK <SEQ ID NO: 28; DNA; Artificial> [IBA032 HC]
CAGGTGCAGCTGCAGCAGAGCGGTGCGGAACTGGTGAAACCGGGTGCGA
GCGTGAAAATGAGCTGCAAAGCGAGCGGCTATAACTTTACAGATTATTG
GATTCACTGGGTGAAAGAACGTCCGGGCCAGGGCCTGGAATGGATTGGC
TATTTTAGTACGCATAGCGATTATGCCATCATTAACCAGAAATTCAGAG
ATAAAGCGACCCTGACCGCGGATAAAAGCAGCCGTCTGGCCTATATGCA
GCTGTCTAGCCTGACCAGCGAAGATAGCGCGATTTATTACTGCGCGCGT
GGCGGCTTAGGCCTGAGCTATTGGGGCCAGGGTACCACGGTCACAGTCT
CCTCAGCCAAAACGACACCCCCATCTGTCTATCCGCTAGCCCCTGGATC
TGCCGCCCAGACCAACAGCATGGTGACCCTGGGCTGTCTGGTGAAGGGC
TACTTCCCTGAGCCTGTGACAGTGACCTGGAACAGCGGCTCTCTGTCTA
GCGGCGTGCACACATTCCCTGCCGTGCTGCAGAGCGACCTGTACACCCT
GAGCAGCAGCGTGACCGTGCCTAGCAGCACATGGCCTAGCGAGACCGTG
ACATGCAACGTGGCCCACCCTGCCTCTTCTACCAAGGTGGACAAGAAGA
TCGTGCCCAGAGACTGCGGCTGCAAGCCTTGCATCTGCACCGTGCCTGA
GGTGAGCAGCGTGTTCATCTTCCCACCCAAGCCCAAGGACGTGCTCACC
ATCACCCTCACCCCCAAGGTCACGTGTGTTGTGGTAGACATCAGCAAGG
ATGATCCCGAGGTCCAGTTCAGCTGGTTTGTAGATGATGTGGAGGTGCA
CACAGCTCAGACGCAACCCCGGGAGGAGCAGTTCAACAGCACTTTCCGC
TCAGTCAGTGAACTTCCCATCATGCACCAGGACTGGCTCAATGGCAAGG
AGTTCAAATGCAGGGTCAACAGTGCAGCTTTCCCTGCCCCCATCGAGAA
AACCATCTCCAAAACCAAAGGCAGACCGAAGGCTCCACAGGTGTACACC
ATTCCACCTCCCAAGGAGCAGATGGCCAAGGATAAAGTCAGTCTGACCT
GCATGATAACAGACTTCTTCCCTGAAGACATTACTGTGGAGTGGCAGTG
GAATGGGCAGCCAGCGGAGAACTACAAGAACACTCAGCCCATCATGGAC
ACAGATGGCTCTTACTTCGTCTACAGCAAGCTCAATGTGCAGAAGAGCA
ACTGGGAGGCAGGAAATACTTTCACCTGCTCTGTGTTACATGAGGGCCT
GCACAACCACCATACTGAGAAGAGCCTCTCCCACTCTCCTGGTAAA <SEQ ID NO: 29; PRT1; Homo sapiens> [glucagon]
HSQGTFTSDYSKYLDSRRAQDFVQWLMNT

We claim:

1. A monoclonal antibody, or antigen-binding fragment thereof, that specifically binds to glucagon consisting of the amino acid sequence HSQGTFTSDYSKYLDSRRAQD-FVQWLMNT (SEQ ID NO: 29), the antibody, or fragment thereof, comprising:

light chain complementarity determining regions LCDR1, LCDR2, and LCDR3 comprising the amino acid sequences KASENAGTYVA (SEQ ID NO: 1), NGSHRYD (SEQ ID NO: 2), and GQSYSYPWT (SEQ ID NO: 3), respectively, and heavy chain complementarity determining regions HCDR1, HCDR2, and HCDR3 comprising the amino acid sequences GYNFNDYWLN (SEQ ID NO: 4), NAYPGWGIINYNEKFKS (SEQ ID NO: 5), and DYDNAY (SEQ ID NO: 6), respectively.

2. The monoclonal antibody, or antigen-binding fragment thereof, of claim 1 comprising:

a light chain variable region (LCVR) comprising the amino acid sequence as in SEQ ID NO: 7, and a heavy chain variable region (HCVR) comprising the amino acid sequence as in SEQ ID NO: 9.

3. The monoclonal antibody, or antigen-binding fragment thereof, of claim 1 comprising:

a light chain comprising the amino acid sequence as in SEQ ID NO: 11, and a heavy chain comprising the amino acid sequence as in SEQ ID NO: 13.

4. The monoclonal antibody, or antigen-binding fragment thereof, of claim 1 comprising two light chains and two heavy chains, wherein each of the light chains consist of the amino acid sequence as in SEQ ID NO: 11 and each of the heavy chains consist of the amino acid sequence as in SEQ ID NO: 13.

5. The monoclonal antibody, or antigen-binding fragment thereof, of claim 1, further comprising a detectable label.

6. The monoclonal antibody, or antigen-binding fragment thereof, of claim 1, wherein said detectable label is selected from the group consisting of a chromophore, a chromogen, a dye, a fluorescent agent, a fluorogenic agent, a phosphorescent agent, a chemiluminescent agent, a bioluminescent agent, a radionuclide, a positron emission tomography-imageable agent, and a magnetic resonance-imageable agent.

7. A composition comprising a monoclonal antibody, or antigen-binding fragment thereof, of claim 1, and a diagnostically acceptable carrier, diluent, or excipient.

8. A method for quantifying the amount of glucagon in serum or plasma comprising:

a. coating a plate or beads with capture antibody IBA009, wherein the antibody may be directly coated, or biotin labeled and coated to streptavidin, neutraavidin or avidin coated beads or plates;

b. blocking the plates, either before or after coating of the capture antibody, with chicken egg ovalbumin, or other non-mammalian protein, dissolved in a suitable buffer;

c. diluting the serum sample to be determined with buffer comprising 4-(2-hydroxyethyl)-1-piperazineethanesulfonic acid (HEPES), ethylenediaminetetraacetic acid (EDTA), ethylene glycol tetraacetic acid (EGTA), Sodium Chloride, Triton X-100, and 1% ovalbumin;

d. contacting the capture antibody coated plate, or beads, with the diluted serum or plasma sample;

e. washing the plate with a suitable wash buffer to remove unbound proteins;

f. contacting the bound glucagon with the second anti-glucagon detection antibody IBA032 that has been detectably labeled;

g. washing the plate with a suitable wash buffer to remove unbound anti-glucagon detection antibody; and h. quantitating the bound label by comparison against a standard curve of known amounts of glucagon.

* * * * *